US009005307B2

(12) United States Patent
Kellar et al.

(10) Patent No.: US 9,005,307 B2

(45) Date of Patent: Apr. 14, 2015

(54) PROSTHETIC BALL-AND-SOCKET JOINT

(75) Inventors: Franz W. Kellar, Gastonia, NC (US); Harold Lloyd Crowder, Jr., Concord, NC (US)

(73) Assignee: Biomedflex, LLC, Gastonia, NC (US)

( * ) Notice: Subject to any disclaimer, the term of this patent is extended or adjusted under 35 U.S.C. 154(b) by 157 days.

(21) Appl. No.: 13/311,119

(22) Filed: Dec. 5, 2011

(65) Prior Publication Data

US 2012/0083896 A1 Apr. 5, 2012

Related U.S. Application Data

(63) Continuation of application No. 13/073,963, filed on Mar. 28, 2011, now Pat. No. 8,070,823, which is a continuation-in-part of application No. 12/826,620, filed on Jun. 29, 2010, now Pat. No. 7,914,580, which (Continued)

(51) Int. Cl.
*A61F 2/30* (2006.01)
*A61F 2/44* (2006.01)

(Continued)

(52) U.S. Cl.
CPC ............... *A61F 2/30767* (2013.01); *A61F 2/32* (2013.01); *A61F 2/34* (2013.01); *A61F 2/36* (2013.01);

(Continued)

(58) Field of Classification Search
CPC ................................ A61F 2/32; A61F 2/4425
USPC .................... 623/16.11, 17.11–17.16, 18.11, 623/19.11–19.14, 20.14–20.15, 623/20.21–20.24, 20.28–20.35, 21.13, 623/21.16–21.18, 22.11, 22.13–22.19, 623/22.21–22.29, 22.3, 23.39–23.41, 23.43
See application file for complete search history.

(56) References Cited

U.S. PATENT DOCUMENTS 3,521,302 A 7/1970 Muller
3,723,995 A 4/1973 Baumann (Continued)

FOREIGN PATENT DOCUMENTS

DE 4102509 7/1992
DE 4102510 7/1992

(Continued)

OTHER PUBLICATIONS

Alvarado et al. “Biomechanics of Hip and Knee Prostheses”. University of Puerto Rico Mayaguez (2003): 1-20.

(Continued)

*Primary Examiner* — Andrew Iwamaye
(74) *Attorney, Agent, or Firm* — Trego, Hines & Ladenheim, PLLC

(57) ABSTRACT

A prosthetic joint includes: (a) first member having a balanced centroidal axis, and comprising a rigid material and a concave interior defining a cup surface, the cup surface including: (i) a cantilevered first flange defining a wear-resistant protruding first contact rim, the first flange being asymmetric relative to the balanced centroidal axis; and (ii) a cantilevered second flange defining a wear-resistant protruding second contact rim; (b) a second member comprising a rigid material with a wear-resistant, convex contact surface; (c) where the first and second contact rims bear against the contact surface of the second member, to transfer loads between the first and second members, while allowing pivoting motion therebetween; and (d) wherein the flanges are shaped and sized so as to deform elastically and permit the first and second contact rims to conform in an irregular shape to the contact surface, when the joint is under load.

21 Claims, 35 Drawing Sheets

Related U.S. Application Data is a continuation-in-part of application No. 12/714, 288, filed on Feb. 26, 2010, now Pat. No. 7,905,919, which is a continuation-in-part of application No. 11/936,601, filed on Nov. 7, 2007.

(60) Provisional application No. 60/864,667, filed on Nov. 7, 2006.

(51) Int. Cl.
*A61F 2/32* (2006.01)
*C23C 30/00* (2006.01)
*A61F 2/34* (2006.01)
*A61F 2/36* (2006.01)
*A61F 2/38* (2006.01)

(52) U.S. Cl.
CPC ............... *A61F 2/3603* (2013.01); *A61F 2/367* (2013.01); *A61F 2/3676* (2013.01); *A61F 2/38* (2013.01); *A61F 2/4425* (2013.01); *A61F 2002/30014* (2013.01); *A61F 2002/30112* (2013.01); *A61F 2002/30153* (2013.01); *A61F 2002/30322* (2013.01); *A61F 2002/30324* (2013.01); *A61F 2002/30571* (2013.01); *A61F 2002/30589* (2013.01); *A61F 2002/3066* (2013.01); *A61F 2002/30673* (2013.01); *A61F 2002/30675* (2013.01); *A61F 2002/30682* (2013.01); *A61F 2002/30878* (2013.01); *A61F 2002/3092* (2013.01); *A61F 2002/30922* (2013.01); *A61F 2002/30929* (2013.01); *A61F 2002/30934* (2013.01); *A61F 2002/30937* (2013.01); *A61F 2002/30955* (2013.01); *A61F 2002/30968* (2013.01); *A61F 2002/30981* (2013.01); *A61F 2002/3446* (2013.01); *A61F 2002/3495* (2013.01); *A61F 2002/3611* (2013.01); *A61F 2002/3895* (2013.01); *A61F 2002/443* (2013.01); *A61F 2230/0004* (2013.01); *A61F 2230/0019* (2013.01); *A61F 2250/0018* (2013.01); *A61F 2250/0026* (2013.01); *A61F 2250/0036* (2013.01); *A61F 2310/00011* (2013.01); *A61F 2310/00179* (2013.01); *A61F 2310/00239* (2013.01); *A61F 2310/0058* (2013.01); *C23C 30/00* (2013.01)

(56) References Cited

U.S. PATENT DOCUMENTS 3,744,061 A 7/1973 Frost
3,842,442 A 10/1974 Kolbel
3,916,451 A 11/1975 Buechel et al.
3,945,739 A 3/1976 Abe
4,031,570 A 6/1977 Frey
4,044,403 A 8/1977 D'Errico
4,123,806 A 11/1978 Amstutz et al.
4,126,924 A 11/1978 Akins et al.
4,159,544 A 7/1979 Termanini
4,224,696 A 9/1980 Murray et al.
4,309,778 A 1/1982 Buechel et al.
4,437,193 A 3/1984 Oh
4,550,450 A 11/1985 Kinnett
4,568,348 A 2/1986 Johnson et al.
4,662,891 A 5/1987 Noiles
4,673,408 A 6/1987 Grobbelaar
4,676,798 A 6/1987 Noiles
4,718,911 A 1/1988 Kenna
4,759,766 A 7/1988 Buettner-Janz et al.
4,795,469 A 1/1989 Oh
4,813,961 A 3/1989 Sostegni
4,878,918 A 11/1989 Tari et al.
4,904,106 A 2/1990 Love
4,919,674 A 4/1990 Schelhas
4,955,919 A 9/1990 Pappas et al.
4,964,865 A 10/1990 Burkhead et al.
4,997,432 A 3/1991 Keller
5,019,105 A * 5/1991 Wiley ........................ 623/22.29
5,061,288 A 10/1991 Berggren et al.
5,062,853 A 11/1991 Forte
5,080,675 A 1/1992 Lawes et al.
5,080,678 A 1/1992 Spotorno et al.
5,092,898 A 3/1992 Bekki et al.
5,095,898 A 3/1992 Don Michael
5,116,375 A 5/1992 Hofmann
5,116,376 A 5/1992 May
5,133,769 A 7/1992 Wagner et al.
5,181,926 A 1/1993 Koch et al.
5,197,987 A 3/1993 Koch et al.
5,314,477 A 5/1994 Marnay
5,358,530 A 10/1994 Hodorek
5,389,107 A 2/1995 Nassar et al.
5,405,394 A 4/1995 Davidson
5,413,604 A 5/1995 Hodge
5,458,650 A 10/1995 Carret et al.
5,462,362 A 10/1995 Yuhta et al.
5,480,442 A 1/1996 Bertagnoli
5,480,446 A 1/1996 Goodfellow et al.
5,480,448 A 1/1996 Mikhail
5,507,816 A 4/1996 Bullivant
5,549,693 A 8/1996 Roux et al.
5,549,695 A 8/1996 Spotorno et al.
5,549,697 A 8/1996 Caldarise
5,549,699 A 8/1996 MacMahon et al.
5,549,700 A 8/1996 Graham et al.
5,593,445 A 1/1997 Waits
5,609,645 A 3/1997 Vinciguerra
5,641,323 A 6/1997 Caldarise
5,674,296 A 10/1997 Bryan et al.
5,676,701 A 10/1997 Yuan et al.
5,676,704 A 10/1997 Ries et al.
5,702,456 A 12/1997 Pienkowski
5,702,470 A 12/1997 Menon
5,702,478 A 12/1997 Tornier
5,725,584 A 3/1998 Walker et al.
5,766,260 A 6/1998 Whiteside
5,782,927 A 7/1998 Klawitter et al.
5,800,555 A 9/1998 Gray et al.
5,824,101 A 10/1998 Pappas
5,824,107 A 10/1998 Tschirren
5,871,542 A 2/1999 Goodfellow et al.
5,871,546 A 2/1999 Colleran et al.
5,879,404 A 3/1999 Bateman et al.
5,879,406 A 3/1999 Lilley
5,879,407 A 3/1999 Waggener
5,893,889 A 4/1999 Harrington
5,916,269 A 6/1999 Serbousek et al.
5,935,174 A 8/1999 Dye
5,935,175 A 8/1999 Ostiguy, Jr. et al.
5,938,702 A 8/1999 Lopez et al.
5,957,979 A 9/1999 Beckman et al.
5,989,293 A 11/1999 Cook et al.
5,989,294 A 11/1999 Marlow
5,997,579 A 12/1999 Albrektsson et al.
6,013,103 A 1/2000 Kaufman et al.
6,042,293 A 3/2000 Maughan
6,059,830 A 5/2000 Lippincott, III et al.
6,080,195 A 6/2000 Colleran et al.
6,096,083 A 8/2000 Keller et al.
6,126,695 A 10/2000 Semlitsch
6,129,765 A 10/2000 Lopez et al.
6,146,421 A 11/2000 Gordon et al.
6,152,961 A 11/2000 Ostiguy, Jr. et al.
6,162,252 A 12/2000 Kuras et al.
6,162,256 A 12/2000 Ostiguy, Jr. et al.
6,179,874 B1 1/2001 Cauthen
6,190,415 B1 2/2001 Cooke et al.
6,203,576 B1 3/2001 Afriat et al.
6,206,929 B1 3/2001 Ochoa et al.
6,217,249 B1 4/2001 Merlo
6,231,264 B1 5/2001 McLaughlin et al.
6,299,646 B1 10/2001 Chambat et al.

(56) References Cited

U.S. PATENT DOCUMENTS 6,364,910 B1 4/2002 Shultz et al.
6,368,350 B1 4/2002 Erickson et al.
6,375,682 B1 4/2002 Fleischmann et al.
6,416,553 B1 7/2002 White et al.
6,425,921 B1 7/2002 Grundei et al.
6,475,243 B1 11/2002 Sheldon et al.
6,494,916 B1 12/2002 Babalola et al.
6,537,321 B1 3/2003 Horber
6,558,427 B2 5/2003 Leclercq et al.
6,626,947 B2 9/2003 Lester et al.
6,660,040 B2* 12/2003 Chan et al. ................ 623/22.21
RE38,409 E 1/2004 Noiles
6,719,800 B2 4/2004 Meyers et al.
6,740,117 B2 5/2004 Ralph et al.
6,740,118 B2 5/2004 Eisermann et al.
6,743,258 B1 6/2004 Keller
6,770,095 B2 8/2004 Grinberg et al.
6,866,685 B2* 3/2005 Chan et al. ................ 623/22.21
6,875,235 B2 4/2005 Ferree
6,893,465 B2 5/2005 Huang
6,896,703 B2 5/2005 Barbieri et al.
6,916,342 B2 7/2005 Frederick et al.
6,942,701 B2 9/2005 Taylor
6,949,105 B2 9/2005 Bryan et al.
6,964,686 B2 11/2005 Gordon
6,972,039 B2 12/2005 Metzger et al.
6,981,989 B1 1/2006 Fleischmann et al.
6,981,991 B2 1/2006 Ferree
6,986,791 B1 1/2006 Metzger
7,001,433 B2 2/2006 Songer et al.
7,022,142 B2 4/2006 Johnson
7,025,787 B2 4/2006 Bryan et al.
7,037,341 B2 5/2006 Nowakowski
7,060,099 B2 6/2006 Carli et al.
7,060,101 B2 6/2006 O'Connor et al.
7,066,963 B2 6/2006 Naegerl
7,083,650 B2 8/2006 Moskowitz et al.
7,083,651 B2 8/2006 Diaz et al.
7,083,652 B2 8/2006 McCue et al.
7,108,719 B2 9/2006 Horber
7,108,720 B2 9/2006 Hanes
7,115,145 B2 10/2006 Richards
7,121,755 B2 10/2006 Schlapfer et al.
7,128,761 B2 10/2006 Kuras et al.
7,153,325 B2 12/2006 Kim et al.
7,153,328 B2 12/2006 Kim
7,160,332 B2 1/2007 Frederick et al.
7,179,294 B2 2/2007 Eisermann et al.
7,214,243 B2 5/2007 Taylor
7,214,244 B2 5/2007 Zubok et al.
7,250,060 B2 7/2007 Trieu
7,267,693 B1 9/2007 Mandell et al.
7,270,679 B2 9/2007 Istephanous et al.
7,276,082 B2 10/2007 Zdeblick et al.
7,297,164 B2 11/2007 Johnson et al.
7,309,363 B2 12/2007 Dietz
7,326,250 B2 2/2008 Beaurain et al.
7,326,252 B2 2/2008 Otto et al.
7,326,253 B2 2/2008 Synder et al.
7,338,529 B1 3/2008 Higgins
7,393,362 B2 7/2008 Cruchet et al.
7,407,513 B2 8/2008 Alleyne et al.
7,442,211 B2 10/2008 de Villiers et al.
7,465,320 B1 12/2008 Kito et al.
7,468,076 B2 12/2008 Zubok et al.
7,468,079 B2 12/2008 Collier
7,470,287 B2 12/2008 Tomier et al.
7,485,145 B2 2/2009 Purcell
7,494,507 B2 2/2009 Dixon et al.
7,531,002 B2 5/2009 Sutton et al.
7,537,615 B2 5/2009 Lemaire
7,550,009 B2 6/2009 Arnin et al.
7,550,010 B2 6/2009 Humphreys et al.
7,572,295 B2 8/2009 Steinberg
7,572,296 B2 8/2009 Scott et al.
7,578,848 B2 8/2009 Albert et al.
7,582,115 B2 9/2009 Weber
7,588,384 B2 9/2009 Yokohara
7,601,174 B2 10/2009 Kelly et al.
7,611,653 B1 11/2009 Elsner et al.
7,618,439 B2 11/2009 Zubok et al.
7,618,459 B2 11/2009 Justin et al.
7,621,956 B2 11/2009 Paul et al.
7,655,041 B2 2/2010 Clifford et al.
7,658,767 B2 2/2010 Wyss
7,682,398 B2 3/2010 Croxton et al.
7,740,659 B2 6/2010 Zarda et al.
7,758,645 B2 7/2010 Studer
7,758,653 B2 7/2010 Steinberg
7,776,085 B2 8/2010 Bernero et al.
7,879,095 B2 2/2011 Pisharodi
7,905,919 B2 3/2011 Kellar et al.
7,914,580 B2 3/2011 Kellar et al.
7,955,395 B2 6/2011 Shea et al.
8,007,539 B2 8/2011 Slone
8,029,574 B2 10/2011 Kellar et al.
8,070,823 B2* 12/2011 Kellar et al. ................ 623/23.4
8,308,812 B2* 11/2012 Kellar et al. ................ 623/23.4
2002/0035400 A1 3/2002 Bryan et al.
2002/0111682 A1 8/2002 Ralph et al.
2002/0143402 A1 10/2002 Steinberg
2002/0147499 A1 10/2002 Shea et al.
2003/0055500 A1 3/2003 Fell et al.
2003/0081989 A1 5/2003 Kondoh
2003/0114935 A1* 6/2003 Chan et al. ................ 623/22.21
2003/0191534 A1 10/2003 Viart et al.
2003/0220691 A1 11/2003 Songer et al.
2004/0010316 A1 1/2004 William et al.
2004/0024460 A1 2/2004 Ferree
2004/0034433 A1 2/2004 Chan et al.
2004/0073311 A1 4/2004 Ferree
2004/0088052 A1* 5/2004 Dearnaley ................ 623/16.11
2004/0093087 A1 5/2004 Ferree et al.
2004/0117021 A1 6/2004 Biedermann et al.
2004/0143332 A1 7/2004 Krueger et al.
2004/0143334 A1 7/2004 Ferree
2004/0167626 A1 8/2004 Geremakis et al.
2004/0167629 A1 8/2004 Geremakis et al.
2004/0172021 A1 9/2004 Khalili
2004/0215345 A1 10/2004 Perrone, Jr. et al.
2004/0220674 A1 11/2004 Pria et al.
2004/0260396 A1 12/2004 Ferree et al.
2004/0267374 A1 12/2004 Friedrichs
2004/0267375 A1 12/2004 Friedrichs
2005/0004572 A1 1/2005 Biedermann et al.
2005/0015152 A1 1/2005 Sweeney
2005/0021145 A1 1/2005 de Villiers et al.
2005/0038516 A1 2/2005 Spoonamore
2005/0055101 A1 3/2005 Sifneos
2005/0071007 A1 3/2005 Malek
2005/0080488 A1 4/2005 Schultz
2005/0113926 A1 5/2005 Zucherman et al.
2005/0113931 A1 5/2005 Horber
2005/0125065 A1 6/2005 Zucherman et al.
2005/0143827 A1 6/2005 Globerman et al.
2005/0165485 A1 7/2005 Trieu
2005/0171604 A1 8/2005 Michalow
2005/0171614 A1 8/2005 Bacon
2005/0192674 A1 9/2005 Ferree
2005/0197706 A1 9/2005 Hovorka et al.
2005/0203626 A1 9/2005 Sears et al.
2005/0216081 A1 9/2005 Taylor
2005/0251261 A1 11/2005 Peterman
2005/0251262 A1 11/2005 de Villiers et al.
2005/0261776 A1 11/2005 Taylor
2005/0288793 A1 12/2005 Dong et al.
2006/0020342 A1 1/2006 Ferree et al.
2006/0025862 A1 2/2006 Villiers et al.
2006/0041314 A1 2/2006 Millard
2006/0064169 A1 3/2006 Ferree
2006/0085076 A1 4/2006 Krishna et al.
2006/0095135 A1 5/2006 Kovacevic
2006/0129240 A1 6/2006 Lessar et al.
2006/0136062 A1 6/2006 DiNello et al.

(56) References Cited

U.S. PATENT DOCUMENTS

| | | | |
|---|---|---|---|
| 2006/0178744 | A1 | 8/2006 | de Villiers et al. |
| 2006/0190079 | A1 | 8/2006 | Istephanous et al. |
| 2006/0200247 | A1 | 9/2006 | Charrois |
| 2006/0217809 | A1 | 9/2006 | Albert et al. |
| 2006/0217815 | A1 | 9/2006 | Gibbs et al. |
| 2006/0235527 | A1 | 10/2006 | Buettner-Janz et al. |
| 2006/0241765 | A1 | 10/2006 | Burn et al. |
| 2006/0241766 | A1 | 10/2006 | Felton et al. |
| 2006/0259147 | A1 | 11/2006 | Krishna et al. |
| 2006/0259148 | A1 | 11/2006 | Bar-Ziv |
| 2006/0271200 | A1 | 11/2006 | Greenlee |
| 2006/0293752 | A1 | 12/2006 | Moumene et al. |
| 2007/0021837 | A1 | 1/2007 | Ashman |
| 2007/0032875 | A1 | 2/2007 | Blacklock et al. |
| 2007/0032877 | A1 | 2/2007 | Whiteside |
| 2007/0050032 | A1 | 3/2007 | Gittings et al. |
| 2007/0073405 | A1 | 3/2007 | Verhulst et al. |
| 2007/0073410 | A1 | 3/2007 | Raugel |
| 2007/0083267 | A1 | 4/2007 | Miz et al. |
| 2007/0100447 | A1 | 5/2007 | Steinberg |
| 2007/0100454 | A1 | 5/2007 | Burgess et al. |
| 2007/0100456 | A1 | 5/2007 | Dooris et al. |
| 2007/0106391 | A1 | 5/2007 | Ronk |
| 2007/0118223 | A1 | 5/2007 | Allard et al. |
| 2007/0123990 | A1 | 5/2007 | Sharifi-Mehr |
| 2007/0156246 | A1 | 7/2007 | Meswania et al. |
| 2007/0168037 | A1 | 7/2007 | Posnick |
| 2007/0173936 | A1 | 7/2007 | Hester et al. |
| 2007/0185578 | A1 | 8/2007 | O'Neil et al. |
| 2007/0208427 | A1 | 9/2007 | Davidson et al. |
| 2007/0213821 | A1 | 9/2007 | Kwak et al. |
| 2007/0219638 | A1 | 9/2007 | Jones et al. |
| 2007/0225806 | A1 | 9/2007 | Squires et al. |
| 2007/0225810 | A1 | 9/2007 | Colleran et al. |
| 2007/0225818 | A1 | 9/2007 | Reubelt et al. |
| 2007/0233244 | A1 | 10/2007 | Lopez et al. |
| 2007/0239276 | A1 | 10/2007 | Squires et al. |
| 2008/0065211 | A1 | 3/2008 | Albert et al. |
| 2008/0065216 | A1 | 3/2008 | Hurlbert et al. |
| 2008/0071381 | A1 | 3/2008 | Buscher et al. |
| 2008/0077137 | A1 | 3/2008 | Balderston |
| 2008/0133017 | A1 | 6/2008 | Beyar et al. |
| 2008/0133022 | A1 | 6/2008 | Caylor |
| 2008/0154263 | A1 | 6/2008 | Janowski et al. |
| 2008/0154369 | A1 | 6/2008 | Barr et al. |
| 2008/0161924 | A1 | 7/2008 | Viker |
| 2008/0161930 | A1 | 7/2008 | Carls et al. |
| 2008/0195212 | A1 | 8/2008 | Nguyen et al. |
| 2008/0215156 | A1 | 9/2008 | Duggal et al. |
| 2008/0221689 | A1 | 9/2008 | Chaput et al. |
| 2008/0221690 | A1 | 9/2008 | Chaput et al. |
| 2008/0228276 | A1 | 9/2008 | Mathews et al. |
| 2008/0228282 | A1 | 9/2008 | Brodowski |
| 2008/0243253 | A1 | 10/2008 | Levieux |
| 2008/0243262 | A1 | 10/2008 | Lee |
| 2008/0243263 | A1 | 10/2008 | Lee et al. |
| 2008/0300685 | A1 | 12/2008 | Carls et al. |
| 2009/0005872 | A1 | 1/2009 | Moumene et al. |
| 2009/0012619 | A1 | 1/2009 | Cordaro et al. |
| 2009/0030521 | A1 | 1/2009 | Lee et al. |
| 2009/0036992 | A1 | 2/2009 | Tsakonas |
| 2009/0043391 | A1 | 2/2009 | de Villiers et al. |
| 2009/0054986 | A1 | 2/2009 | Cordaro et al. |
| 2009/0062920 | A1 | 3/2009 | Tauber |
| 2009/0076614 | A1 | 3/2009 | Arramon |
| 2009/0082867 | A1 | 3/2009 | Sebastian Bueno et al. |
| 2009/0082873 | A1 | 3/2009 | Hazebrouck et al. |
| 2009/0088865 | A1 | 4/2009 | Brehm |
| 2009/0105758 | A1 | 4/2009 | Gimbel et al. |
| 2009/0125111 | A1 | 5/2009 | Copf, Jr. |
| 2009/0138090 | A1 | 5/2009 | Hurlbert et al. |
| 2009/0157185 | A1 | 6/2009 | Kim |
| 2009/0192616 | A1 | 7/2009 | Zielinski |
| 2009/0192617 | A1 | 7/2009 | Arramon et al. |
| 2009/0215111 | A1 | 8/2009 | Veenstra et al. |
| 2009/0222089 | A1 | 9/2009 | Hauri et al. |
| 2009/0234458 | A1 | 9/2009 | de Villiers et al. |
| 2009/0248161 | A1 | 10/2009 | Theofilos et al. |
| 2009/0265009 | A1 | 10/2009 | Ward et al. |
| 2009/0270986 | A1 | 10/2009 | Christensen |
| 2009/0276051 | A1 | 11/2009 | Arramon et al. |
| 2009/0281629 | A1 | 11/2009 | Roebling et al. |
| 2009/0306784 | A1 | 12/2009 | Blum |
| 2009/0306785 | A1 | 12/2009 | Farrar et al. |
| 2009/0326656 | A1 | 12/2009 | De Villiers et al. |
| 2009/0326663 | A1 | 12/2009 | Dun |
| 2009/0326664 | A1 | 12/2009 | Wagner et al. |
| 2009/0326665 | A1 | 12/2009 | Wyss et al. |
| 2009/0326666 | A1 | 12/2009 | Wyss et al. |
| 2009/0326668 | A1 | 12/2009 | Dun |
| 2010/0004746 | A1 | 1/2010 | Arramon |
| 2010/0030335 | A1 | 2/2010 | Arramon |
| 2010/0063589 | A1 | 3/2010 | Tepic |
| 2010/0063597 | A1 | 3/2010 | Gradel |
| 2010/0100189 | A1 | 4/2010 | Metzger |
| 2010/0100191 | A1 | 4/2010 | May et al. |
| 2010/0131073 | A1 | 5/2010 | Meridew et al. |
| 2010/0161064 | A1 | 6/2010 | Kellar et al. |
| 2010/0161072 | A1 | 6/2010 | Drescher |
| 2010/0191342 | A1 | 7/2010 | Byrd et al. |
| 2010/0262250 | A1 | 10/2010 | Kellar et al. |
| 2010/0268340 | A1 | 10/2010 | Capote et al. |
| 2010/0292794 | A1 | 11/2010 | Metz-Stavenhagen |
| 2010/0331993 | A1 | 12/2010 | Gradl |
| 2011/0009975 | A1 | 1/2011 | Allen et al. |
| 2011/0015752 | A1 | 1/2011 | Meridew |
| 2011/0087333 | A1 | 4/2011 | Kellar et al. |
| 2011/0166671 | A1 | 7/2011 | Kellar et al. |
| 2011/0190901 | A1 | 8/2011 | Weissberg et al. |
| 2011/0276146 | A1* | 11/2011 | Segal et al. .................. 623/23.4 |
| 2012/0083896 | A1 | 4/2012 | Kellar et al. |
| 2012/0265318 | A1* | 10/2012 | Forsell ....................... 623/22.15 |

FOREIGN PATENT DOCUMENTS

| | | |
|---|---|---|
| DE | 4423020 | 1/1996 |
| DE | 10164328 | 7/2003 |
| DE | 202008004709 | 7/2008 |
| EP | 46926 | 3/1982 |
| EP | 636353 | 2/1995 |
| EP | 648478 | 4/1995 |
| EP | 974316 | 1/2000 |
| EP | 1114624 | 7/2001 |
| EP | 1508315 | 2/2005 |
| EP | 2158879 | 3/2010 |
| FR | 2750036 | 12/1997 |
| FR | 2805456 | 8/2001 |
| FR | 2883723 | 10/2006 |
| FR | 2897528 | 8/2007 |
| FR | 2936145 | 3/2010 |
| GB | 1322680 | 7/1973 |
| GB | 1417407 | 12/1975 |
| GB | 1527498 | 10/1978 |
| GB | 1528906 | 10/1978 |
| GB | 2191402 | 12/1987 |
| JP | 2004011782 | 1/2004 |
| JP | 2004169820 | 6/2004 |
| RU | 2121319 | 11/1998 |
| WO | 9523566 | 9/1995 |
| WO | 9604867 | 2/1996 |
| WO | 9716138 | 5/1997 |
| WO | 9738650 | 10/1997 |
| WO | 0023015 | 4/2000 |
| WO | 03049649 | 6/2003 |
| WO | 2004066882 | 8/2004 |
| WO | 2005039455 | 5/2005 |
| WO | 2006069465 | 7/2006 |
| WO | 2007087730 | 8/2007 |
| WO | 2008088777 | 7/2008 |
| WO | 2008094260 | 8/2008 |
| WO | 2009094477 | 7/2009 |
| WO | 2009105884 | 9/2009 |
| WO | 2009121450 | 10/2009 |

(56) References Cited

FOREIGN PATENT DOCUMENTS

| | | |
|---|---|---|
| WO | 2009126908 | 10/2009 |
| WO | 2010095125 | 8/2010 |
| WO | 2011011340 | 1/2011 |

OTHER PUBLICATIONS

Wang, W., Wang, F., Jin, Z., Dowson, D., Hu, Y., "Numerical Lubrication Simulation of Metal-on-Metal Artificial 1 Hip Joint Replacements: Ball-in-Socket Model and Ball-on-Plane Model", vol. 223 Part J, 2009, pp. 1073-1082, Journal Engineering Tribology, [online] [retrieved Mar. 28, 2011].

Wang, F., Jin, Z., "Effect of Non-Spherical Bearing Geometry on Transient Elastohydrodynamic Lubrication in Metal-on-Metal Hip Joint Replacements", vol. 221, Part J, 2007, pp. 379-389, "Journal of Engineering Tribology", [online] D [retrieved Mar. 28, 2011].

Wang, F., Brockett, C., Williams, S., Udofia, I., Fisher, J., Jin, Z., "Lubrication and Friction Prediction in Metal-on-Metal Hip Implants", vol. 53, Jan. 2008, pp. 1277-1293, "Phys. Med. Biol." , United Kingdom. D.

Clarke, I., "Role of Ceramic Implants: Design and Clinical Success with Total Hip Prosthetic Ceramic-to-Ceramic Bearings", No. 282, Sep. 1992, pp. 19-30, "Clinical Orthopeadics and Related Research", Kinamed, Inc., Newbury Park, California.

Gardelin, P., Seminario, J., Corradini, C., Fenollosa Gomez, J., "Total Hip Prostheses with Cup and Ball in Ceramic and Metal Sockets", vols. 192-195, 2001, pp. 983-988, "Key Engineering Materials", Trans Tech Publications, Switzerland.

Bruckmann, H., Keuscher, G., Huttinger, K., "Carbon, A Promising Material in Endoprosthetics. Part 2: Tribological Properties", vol. 1, Apr. 1980, pp. 73-81, "Biomaterials", IPC Business Press, West Germany. D.

Jalali-Vahid, D., Jagatia, M., Jin, Z., Dowson, D., "Prediction of Lubricating Film Thickness in UHMWPE Hip Joint Replacements", vol. 34, 2001, pp. 261-266, "Journal of Biomechanics", Elsevier Science Ltd., United Kingdom.

Minns, R.J., Campbell, J., "The 'Sliding Meniscus' Knee Prosthesis: Design Concepts", vol. 8, no. 4, Oct. 1979, pp. 201-205, "Engineering in Medicine", London, England.

Swanson, S., "The State of the Art in Joint Replacement, Part 2: Present Practice and Results", pp. 335-339, Nov. 1977, "Journal of Medical Engineering and Technology", London, United Kingdom.

Faizan, Ahmad, Goei, Vijay K., Garfin, Steven R., Bono, Christopher M., Serhan, Hassan, Biyani, Ashok, Eigafy, Hossein, Krishna, Manoj, Friesem, Tai, "Do Design Variations in the Artificial Disc Influence Cervical Spine Biomechanics? A Finite Element Investigation", Engineering Center for Orthopaedic Research Exellence (E-O CORE), Departments of Bioengineering and Orthopaedic Surgery, 5046 NI, MS 303, Colleges of Engineering and Medicine, University of Toledo, Toledo, Ohio 43606, USA, Published online: 2009-11-21.

Post, Zachary D., Matar, Wadih Y., Van de Leur, Tim, Grossman, Eric L., Austin, Matthew S.,."Mobile-Bearing Total Knee Arthroplasty", vol. 25, No. 6, 2010, pp. 998-1003, "Journal of Arthroplasty", Philadelphia, Pennsylvania.

Fregly, Benjamin, J., Bei, Yanhong, Sylvester, Mark E., "Experimental Evaluation of an Elastic Foundation 3 Model to Predict Contact Pressures in Knee Replacements", vol. 36, No. 11, Nov. 2003, pp. 1659-1668, "Journal D of Biomechanics", Gainesville, Florida.

Strickland, M.A., Taylor, M., "In-Silico Wear Prediction for Knee Replacements—Methodology and Corroboration", vol. 42, No. 10, Jul. 2009, "Journal of Biomechanics", Southampton, United Kingdom.

Halloran, Jason P., Easley, Sarah K., Patrella, Anthony J., Rullkoetier, Paul J., "Comparison of Deformable and Elastic Foundation Finite Element Simulations for Predicting Knee Replacement Mechanics", vol. 127, No. 5, Oct. 2005, pp. 813-818, "Journal of Biomechanical Engineering", Denver, Colorado.

Guerinot, Alexandre, E., Magleby, Spencer, P. Howell, Larry L., "Preliminary Design Concepts for Compliant Mechanism Prosthetic Knee Joints", vol. 2B, pp. 1103-1111, 2004, "Proceedings of the ASME Design Engineering Technical Conference", Provo, Utah.

Walker, Peter, S., Sathasivam, Shivani, "The Design of Guide Surfaces for Fixed-Bearing and Mobile-Bearing Knee Replacements", vol. 32, No. 1, pp. 27-34, Jan. 1999, "Journal of Biomechanics", Middlesex, United Kingdom.

Wenzel, Sa and Shepherd, D.Et, "Contact Stresses in lumbar Total Disc Arthroplasty", vol. 17, No. 3, 2007, pp. 169-173, "Bio-medical Materials and Engineering", Edgbaston, UK.

Clewiow, J.P., Pylios, T. and Shepherd, D.Et, "Soft layer Bearing Joins for Spine Arthroplasty", vol. 29, No. 10, Dec. 2008, pp. 1981-1985, "Materials and Design", Edgabaston, UK.

Parea, Philippe E., Chana, Frank W., Bhatiacharyab, Sanghita and Goeib, Vijay K., "Surface Slide Track Mapping of Implants for Total Disc Arthroplasty", vol. 42, No. 2, Jan. 19, 2009, pp. 131-139, "Journal of Biomechanics", [online] [retrieved Feb. 19, 2010].

Dooris, Andrew P., Goei, Vijay K., Todd, Dwight T., Grosland, Nicole M., Wilder, David G., "Load Sharing in a Lumbar Motion Segment Implanted with an Artificial Disc Under Combined Sagittal Plane Loading", BED—vol. 42, 1999, pp. 277-278, American Society of Mechanical Engineers, Iowa City, Iowa.

Walter, A., Plitz, W., "Wear Characteristics of Ceramic-to-Ceramic Hip Joint Endoprostheses", Transactions of the Annual Meeting of the Society for Biomaterials in Conjunction with the Interna, vol. 8, p. 178, Apr. 19S5, Conference: Transactions of the Eleventh Annual Meeting of the Society for Biomaterials, in Conjunction with the Seventeenth International Biomaterials Symposium, Published by Society for Biomaterials, San Antonio, Texas.

Huttinger, K.J., Bruckmann, H., Redig, H., Weber, U., "Development and Clinical Testing of Carbon 1 Implants for Orthopedic Surgery", Schunk and Ebe G.m.b.H., Giessen (Germany, F.R.), Bundesministerium fuer Forschung and Technologie, Bonn-Bad Godesberg (Germany, F. R.), p. 112, Jan. 1981.

St. John, K.R., Zardiackas, L.D., Poggie, RA, "Wear Evaluation of Cobalt-Chromium Alloy for Use in a Metal-on-Metal Hip Prosthesis", vol. 68, pp. 1-14, Jan. 15, 2004, "Journal of Biomedical Materials Research, Part B, Applied Biomaterials", Wiley Periodicals, United States.

Scholes, S.C., Burgess, I.C., Marsden, H.R., Unsworth, A., Jones, E., Smith, N., "Compliant Layer Acetabular Cups: Friction Testing of a Range of Materials and Designs for a New Generation of Prosthesis that Mimics the Natural Joint", vol. 220, pp. 583-96, Jul. 2006, "Proceedings of the Institution of Mechanical Engineers, Part H", Journal of Engineering in Medicine, United Kingdom.

Gao, L., Wang, F., Yang, R. Jin, Z., "Effect of 3D Physiological Loading and Motion on Elastohydrodynamic Lubrication of Metal-on-Metal Total Hip Replacements", vol. 31, pp. 720-729, 2009, "Medical Engineering and Physics".

* cited by examiner

FIG. 26
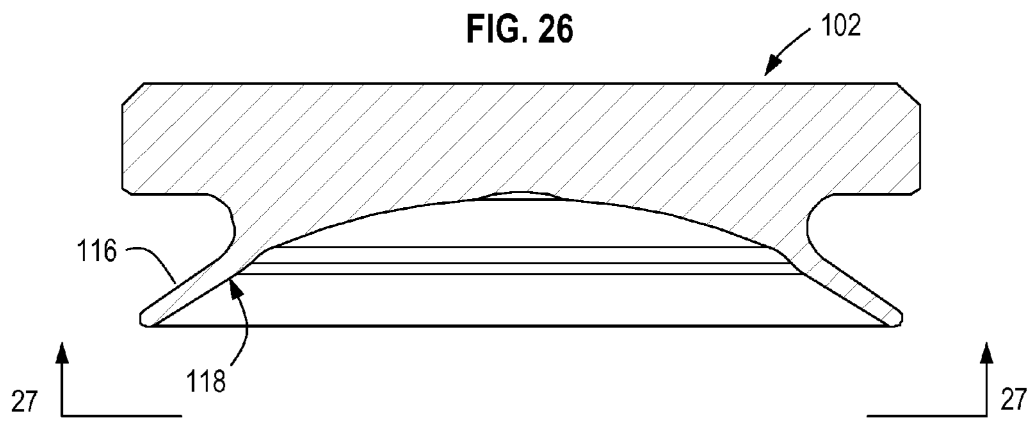
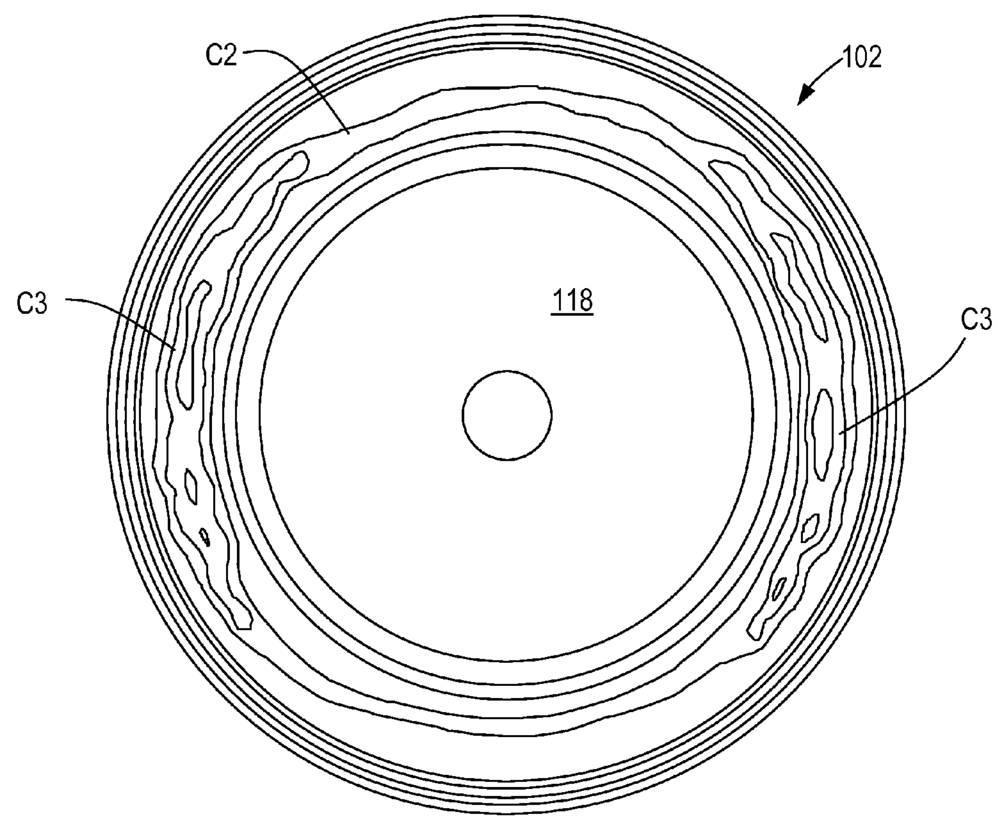
FIG. 27

PROSTHETIC BALL-AND-SOCKET JOINT

CROSS-REFERENCE TO RELATED APPLICATIONS

This application is a Continuation of application Ser. No. 13/073,963, filed Mar. 28, 2011, now U.S. Pat. No. 8,070,823, which is a Continuation-in-Part of application Ser. No. 12/826,620, filed Jun. 29, 2010, now U.S. Pat. No. 7,914,580, which is a Continuation-in-Part of application Ser. No. 12/714,288, filed Feb. 26, 2010, now U.S. Pat. No. 7,905,919, which is a Continuation-in-Part of application Ser. No. 11/936,601, filed Nov. 7, 2007, currently pending, which claims the benefit of Provisional Patent Application 60/864, 667, filed Nov. 7, 2006.

BACKGROUND OF THE INVENTION

This invention relates generally to medical implants, and more particularly to prosthetic joints having conformal geometries and wear resistant properties.

Medical implants, such as knee, hip, and spine orthopedic replacement joints and other joints and implants have previously consisted primarily of a hard metal motion element that engages a polymer contact pad. This has usually been a high density high wear resistant polymer, for example Ultra-High Molecular Weight Polyethylene (UHMWPE), or other resilient material. The problem with this type of configuration is the polymer eventually begins to degrade due to the caustic nature of blood, the high impact load, and high number of load cycles. As the resilient member degrades, pieces of polymer may be liberated into the joint area, often causing accelerated wear, implant damage, and tissue inflammation and harm.

It is desirable to employ a design using a hard member on a hard member (e.g. metals or ceramics), thus eliminating the polymer. Such a design is expected to have a longer service life. Extended implant life is important as it is now often required to revise or replace implants. Implant replacement is undesirable from a cost, inconvenience, patient health, and resource consumption standpoint.

Implants using two hard elements of conventional design will be, however, subject to rapid wear. First, a joint having one hard, rigid element on another will not be perfectly shaped to a nominal geometry. Such imperfections will result in points of high stress, thus causing localized wear. Furthermore, two hard elements would lack the resilient nature of a natural joint. Natural cartilage has a definite resilient property, absorbing shock and distributing periodic elevated loads. This in turn extends the life of a natural joint and reduces stress on neighboring support bone and tissue. If two rigid members are used, this ability to absorb the shock of an active lifestyle could be diminished. The rigid members would transmit the excessive shock to the implant to bone interface. Some cyclical load in these areas stimulates bone growth and strength; however, excessive loads or shock stress or impulse loading the bone-to-implant interface will result in localized bone mass loss, inflammation, and reduced support.

BRIEF SUMMARY OF THE INVENTION

These and other shortcomings of the prior art are addressed by the present invention, which provides a prosthetic joint having wear-resistant contacting surfaces with conformal properties.

According to one aspect of the invention, a prosthetic joint includes: (a) first member having a balanced centroidal axis, the first member comprising a rigid material and including a concave interior defining a cup surface, the cup surface including: (i) a cantilevered first flange defining a wear-resistant first contact rim which protrudes relative a nominal profile of the cup surface, the first flange being asymmetric relative to the balanced centroidal axis; and (ii) a cantilevered second flange defining a wear-resistant second contact rim which protrudes relative to the nominal profile of the cup surface; (c) where the first and second contact rims bear directly against the contact surface of the second member, so as to transfer axial and lateral loads between the first and second members, while allowing pivoting motion between the first and second members; and (d) wherein the flanges are shaped and sized so as to deform elastically and permit the first and second contact rims to conform in an irregular shape to the contact surface, when the joint is placed under a predetermined load.

BRIEF DESCRIPTION OF THE DRAWINGS

The invention may be best understood by reference to the following description taken in conjunction with the accompanying drawing figures in which:

FIG. 26 is a cross-sectional view of one of the joint members shown in FIG. 24;

FIG. 27 is a contact stress plot of the joint member shown in FIG. 26;

DETAILED DESCRIPTION OF THE INVENTION

The present invention provides a specialized implant contact interface (implant geometry). In this geometry, an implanted joint includes two typically hard (i.e. metal or ceramic) members; however, at least one of the members is formed such that it has the characteristics of a resilient member, such as: the ability to absorb an impact load; the ability to absorb high cycle loading; the ability to be self-cleaning; and the ability to function as a hydrodynamic and/or hydrostatic bearing.

Generally, the contact resilient member is flexible enough to allow elastic deformation and avoid localized load increases, but not so flexible as to risk plastic deformation, cracking and failure. In particular, the resilient member is designed such that the stress levels therein will be below the high-cycle fatigue endurance limit. As an example, the resilient member might be only about 10% to about 20% as stiff as a comparable solid member. It is also possible to construct the resilient member geometry with a variable stiffness, i.e. having a low effective spring rate for small deflections and a higher rate as the deflections increase, to avoid failure under sudden heavy loads.

Figure 1:
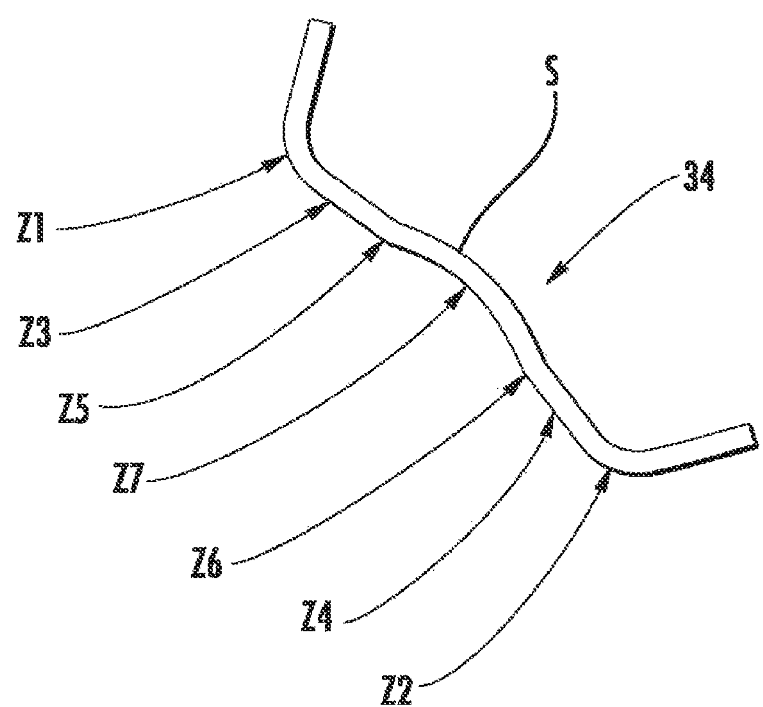
FIG. 1 is a cross-sectional view of a portion of a resilient contact member constructed in accordance with the present invention.

FIG. 1 illustrates an exemplary contact member 34 including a basic resilient interface geometry. The contact member 34 is representative of a portion of a medical implant and is made of one or more metals or ceramics (for example, partially stabilized Zirconia). It may be coated as described below. The geometry includes a lead-in shape, Z1 and Z2, a contact shape, Z3 and Z4, a lead-out shape, Z5 and Z6, and a relieved shape, Z7. It may be desired to vary the cross-sectional thickness to achieve a desired mechanical stiffness to substrate resilience characteristic. The presence of the relieved region Z7 introduces flexibility into the contact member 34, reduces the potential for concentrated point contact with a mating curved member, and provides a reservoir for a working fluid.

The Z7 region may be local to the contact member 34 or may be one of several. In any case, it may contain a means of providing fluid pressure to the internal contact cavity to produce a hydrostatic interface. A passive (powered by the regular motion of the patient) or active (powered by micro components and a dedicated subsystem) pumping means and optional filtration may be employed to provide the desired fluid interaction.

A hydrodynamic interface is desirable as, by definition, it means the contact member 34 is not actually touching the mating joint member. The lead-in and lead-out shapes Z1, Z2, Z5, Z6 are configured to generate a shear stress in the working fluid so as to create the fluid "wedge" of a hydrodynamic support.

Figure 2:
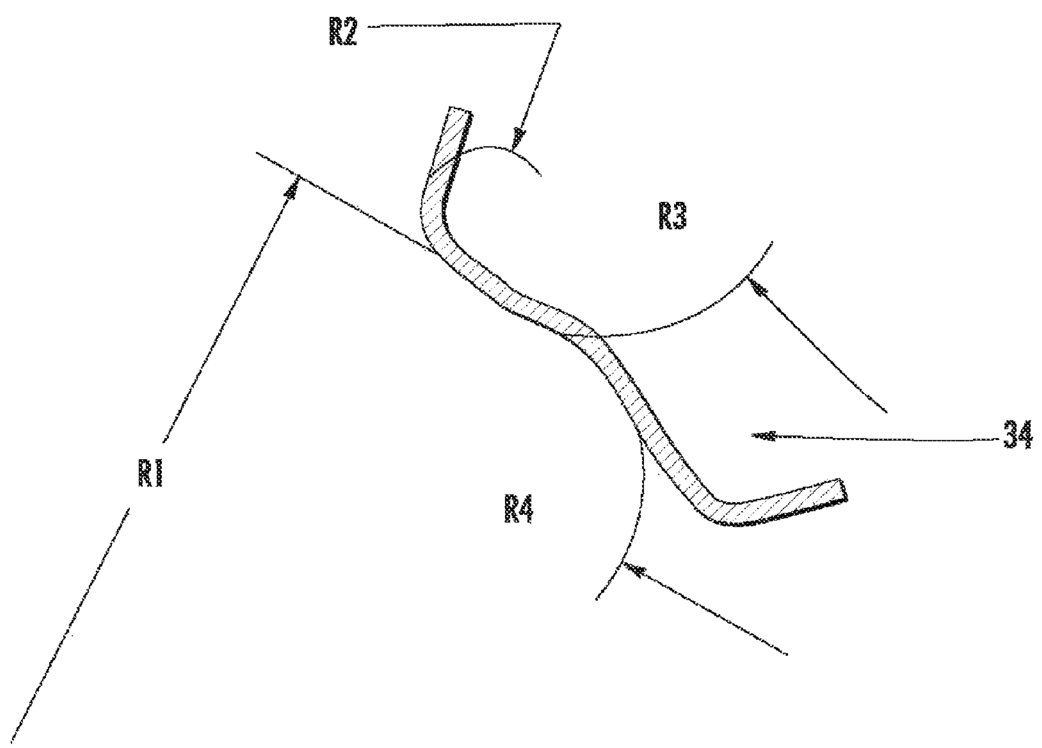
FIG. 2 is an enlarged view of the contact member of FIG. 1 in contact with a mating joint member.
Figure 3:
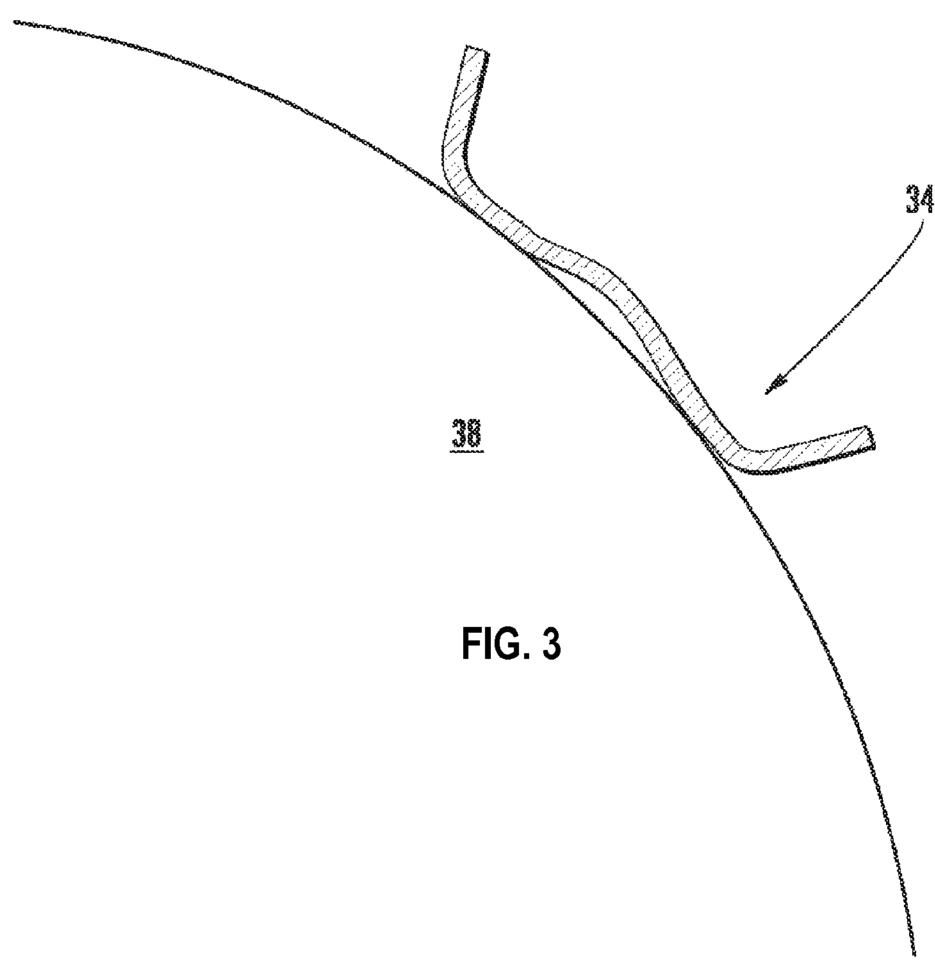
FIG. 3 is a side view of a resilient contact member in contact with a mating joint member.

FIG. 2 shows a closer view of the contact member 34. It may be desirable to make the contact radius (Z3 and Z4) larger or smaller, depending on the application requirement and flexural requirement. For example, FIG. 3 illustrates the contact member 34 in contact with a mating joint member 38 having a substantially larger radius than the contact member 34. The radius ratio between the two joint members is not particularly critical, so long as one of the members exhibits the resilient properties described herein.

The contact member 34 includes an osseointegration surface "S", which is a surface designed to be infiltrated by bone growth to improve the connection between the implant and the bone. Osseointegration surfaces may be made from materials such as TRABECULAR METAL, textured metal, or sintered or extruded implant integration textures. TRABECULAR METAL is an open metal structure with a high porosity (e.g. about 80%) and is available from Zimmer, Inc., Warsaw, Ind. 46580 USA.

Figure 4:
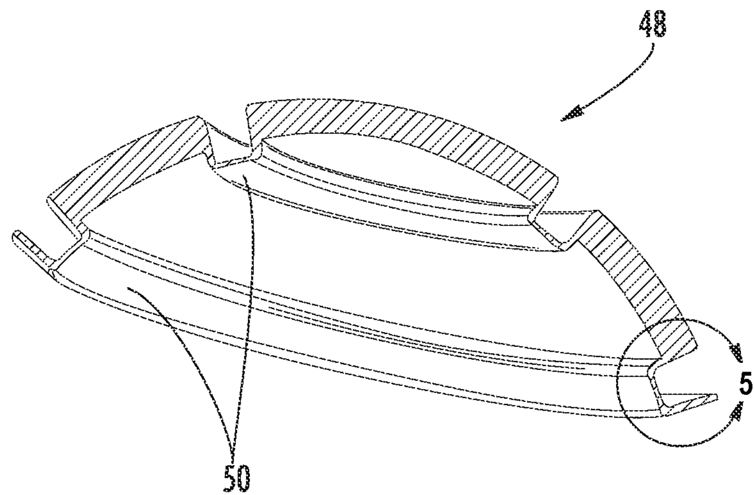
FIG. 4 is a cross-sectional view of a cup for an implant according to an alternate embodiment of the invention.
Figure 5:
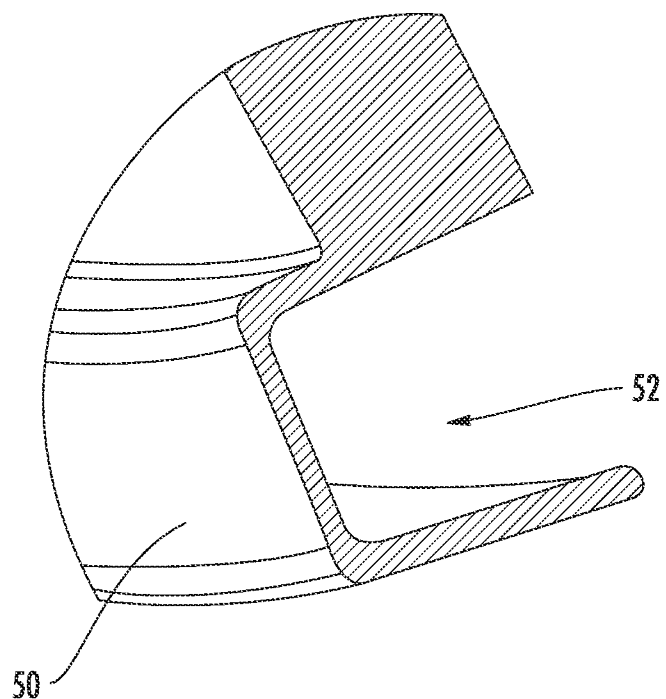
FIG. 5 is an enlarged view of a portion of the cup of FIG. 4.
Figure 6:
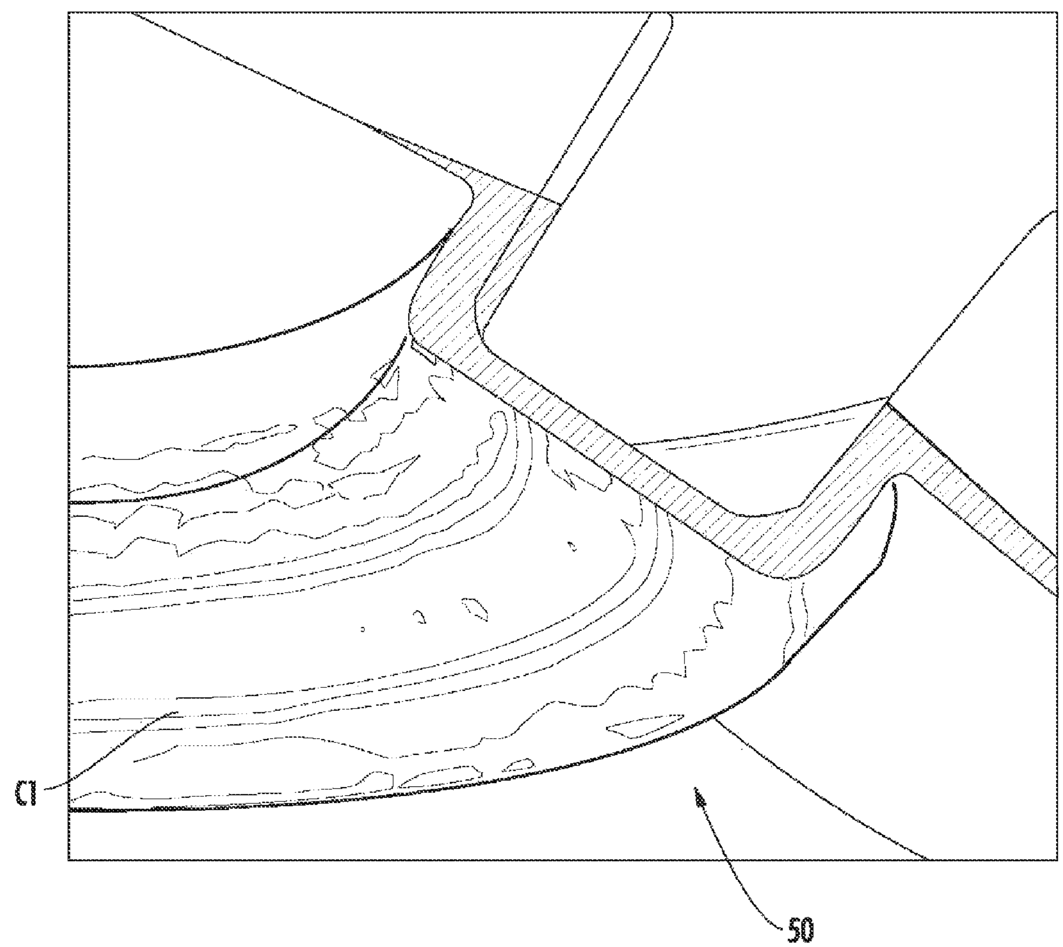
FIG. 6 is a perspective view of a finite element model of a joint member.

FIGS. 4 and 5 illustrate a cup 48 of metal or ceramic with two integrally-formed contact rings 50. More contact rings may be added if needed. As shown in FIG. 5, the volume behind the contact rings 50 may be relieved. This relieved area 52 may be shaped so as to produce a desired balance between resilience and stiffness. A varying cross-section geometry defined by varying inner and outer spline shapes may be desired. In other words, a constant thickness is not required. A material such as a gel or non-Newtonian fluid (not shown) may be disposed in the relieved area 52 to modify the stiffness and damping characteristics of the contact rings 50 as needed for a particular application. The cup 48 could be used as a stand-alone portion of a joint, or it could be positioned as a liner within a conventional liner. The contact ring 50 is shown under load in FIG. 6, which depicts contour lines of highest compressive stress at "C1". This is the portion of the contact ring 50 that would be expected to undergo bending first. The bearing interface portion of the resilient contact member could be constructed as a bridge cross-section supported on both sides as shown or as a cantilevered cross-section depending on the desired static and dynamic characteristics.

Figure 8:
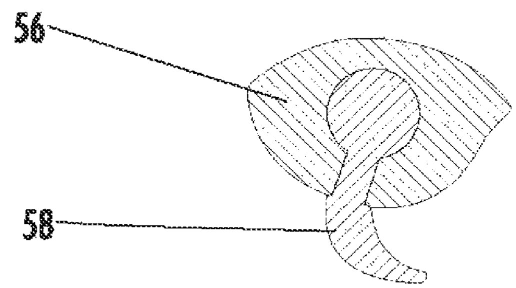
FIG. 8 is an enlarged view of a portion of FIG. 7.
Figure 7:
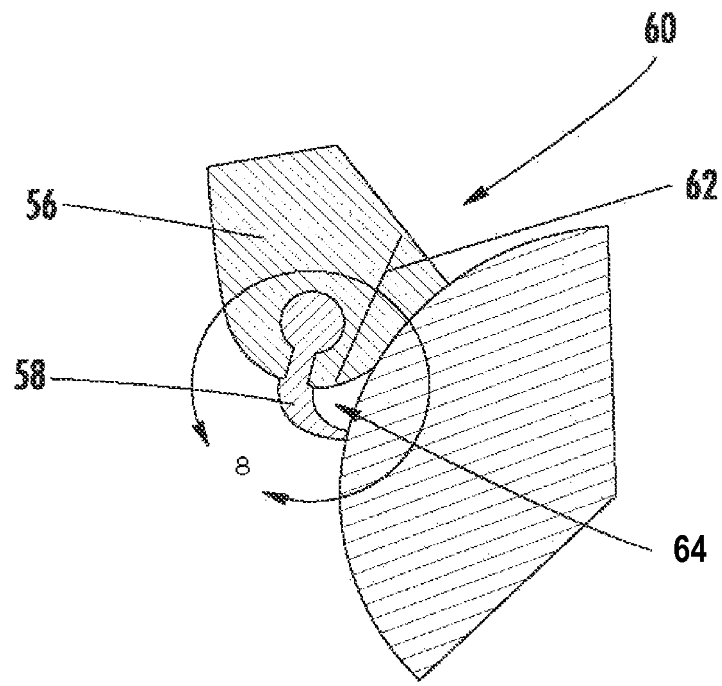
FIG. 7 is a cross-sectional view of an implant joint including a flexible seal.
Figure 9:
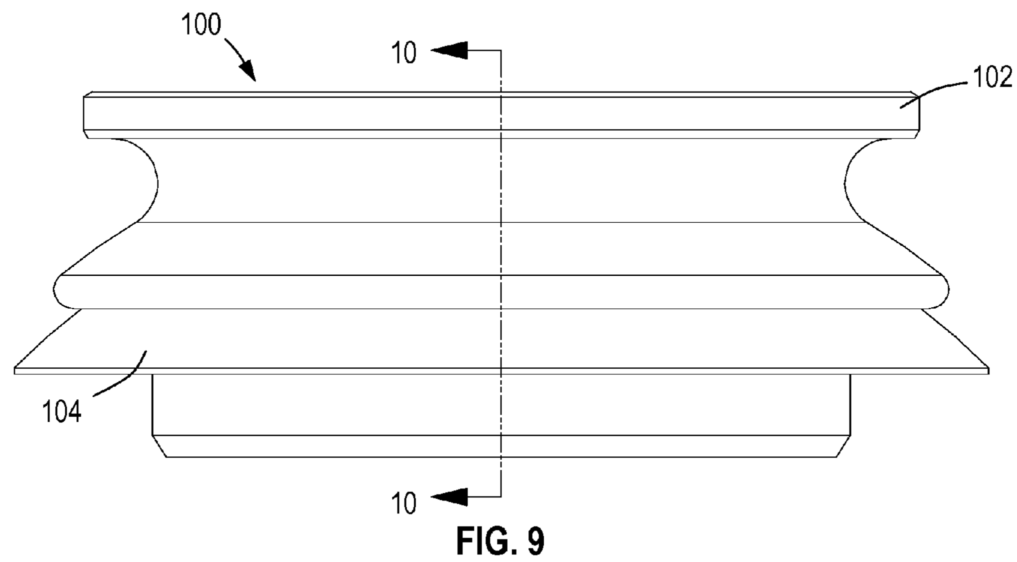
FIG. 9 is a side view of a prosthetic joint constructed in accordance with an aspect of the present invention.

FIGS. 7 and 8 illustrate an implant 56 of rigid material which includes a wiper seal 58. The wiper seal 58 keeps particles out of the contact area (seal void) 60 of the implant 58, and working fluid (natural or synthetic) in. The seal geometry is intended to be representative and a variety of seal characteristics may be employed; such as a single lip seal, a double or multiple lip seal, a pad or wiper seal made from a variety of material options. Different seal mounting options may be used, for example a lobe in a shaped groove as shown in FIGS. 7 and 8, a retaining ring or clamp, or an adhesive. The wiper seal 58 may also be integrated into the contact face of the interface zone.

It may be desirable to create a return passage 62 from the seal void region 60 back into the internal zone 64 in order to stabilize the pressure between the two and to allow for retention of the internal zone fluid if desired. This is especially relevant when the hydrostatic configuration is considered.

Figure 10:
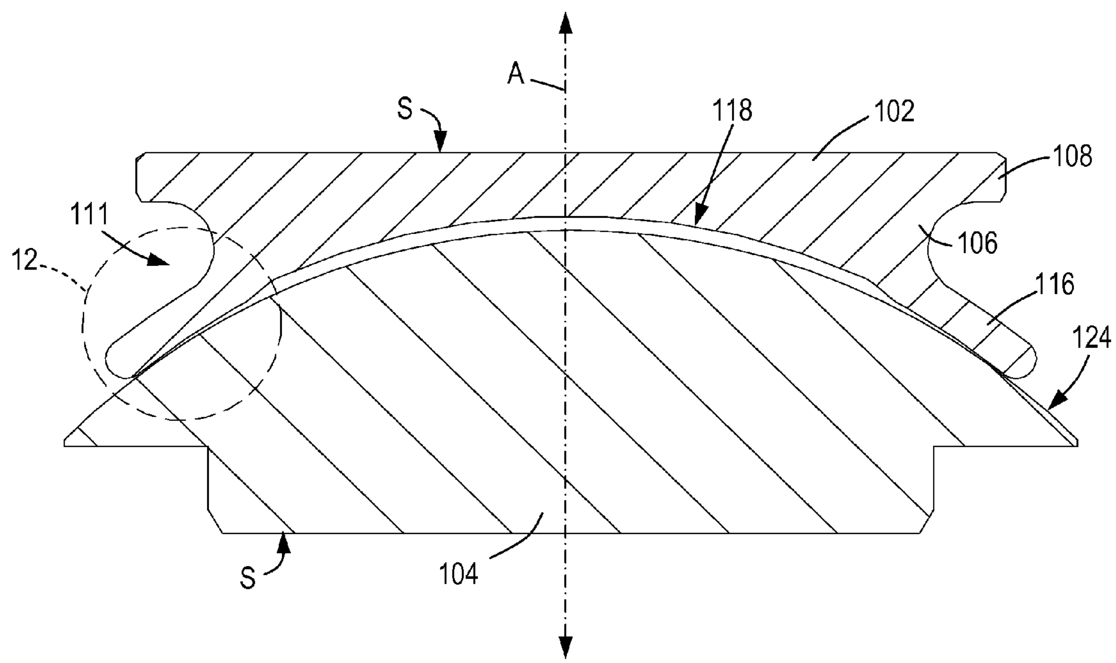
FIG. 10 is a cross-sectional view of the prosthetic joint of FIG. 9 in an unloaded condition.
Figure 11:
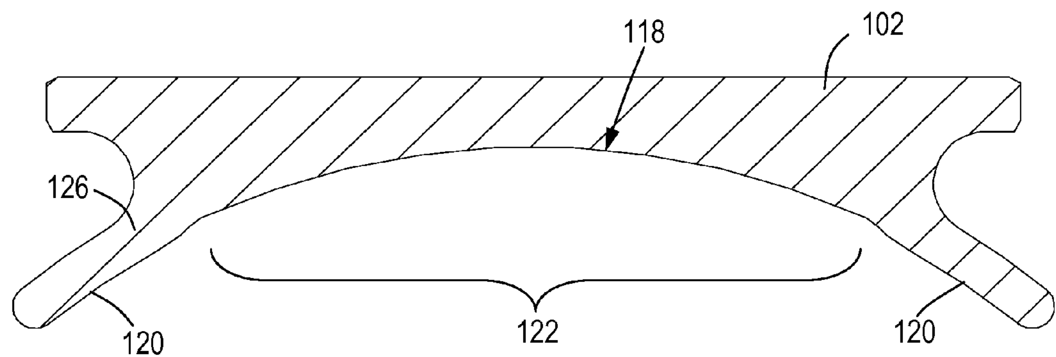
FIG. 11 is a cross-sectional view of one of the members of the prosthetic joint of FIG. 9.

FIGS. 9-14 illustrate a prosthetic joint 100 comprising first and second members 102 and 104. The illustrated prosthetic joint 100 is particularly adapted for a spinal application, but it will be understood that the principles described herein may be applied to any type of prosthetic joint. Both of the members 102 and 104 may be bone-implantable, meaning they include osseointegration surfaces, labeled "S", which are surfaces designed to be infiltrated by bone growth to improve the connection between the implant and the bone. Osseointegration surfaces may be made from materials such as TRABECULAR METAL, textured metal, or sintered or extruded implant integration textures, as described above. As shown in FIG. 10, a central axis "A" passes through the centers of the first and second members 102 and 104 and is generally representative of the direction in which external loads are applied to the joint 100 in use. In the illustrated examples, the first and second joint members are bodies of revolution about this axis, but the principles of the present invention also extend to shapes that are not bodies of revolution.

The first member 102 includes a body 106 with a perimeter flange 116 extending in a generally radially outward direction at one end. Optionally, a disk-like base 108 may be disposed at the end of the body 106 opposite the flange 116, in which case a circumferential gap 111 will be defined between the base 106 and the flange 116. The first member 102 is constructed from a rigid material. As used here, the term "rigid" refers to a material which has a high stiffness or modulus of elasticity. Nonlimiting examples of rigid materials having appropriate stiffness for the purpose of the present invention include stainless steels, cobalt-chrome alloys, titanium, aluminum, and ceramics. By way of further example, materials such as polymers would generally not be considered "rigid" for the purposes of the present invention. Generally, a rigid material should have a modulus of elasticity of about $0.5\times10^6$ psi or greater. Collectively, one end of the body 106 and the flange 116 define a wear-resistant, concave first contact surface 118. As used herein, the term "wear-resistant" refers to a material which is resistant to surface material loss when placed under load. Generally the wear rate should be no more than about 0.5 μm (0.000020 in.) to about 1.0 μm (0.000040 in.) per million cycles when tested in accordance with ASTM Guide F2423. As a point of reference, it is noted that any of the natural joints in a human body can easily experience one million operating cycles per year. Nonlimiting examples of wear-resistant materials include solid metals and ceramics. Known coatings such as titanium nitride, chrome plating, carbon thin films, and/or diamond-like carbon coatings may be used as a face layer to impart wear resistance to the first contact surface 118. Optionally, the first contact surface 118 could comprise a substantially thicker face layer (not shown) of a wear-resistant material such as ultra-high molecular weight (UHMW) polyethylene.

Figure 14:
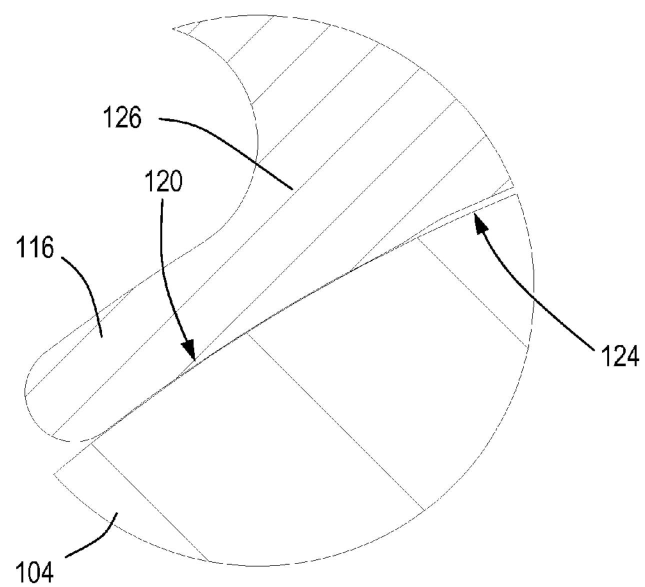
FIG. 14 is an enlarged view of a portion of FIG. 13.
Figure 15:
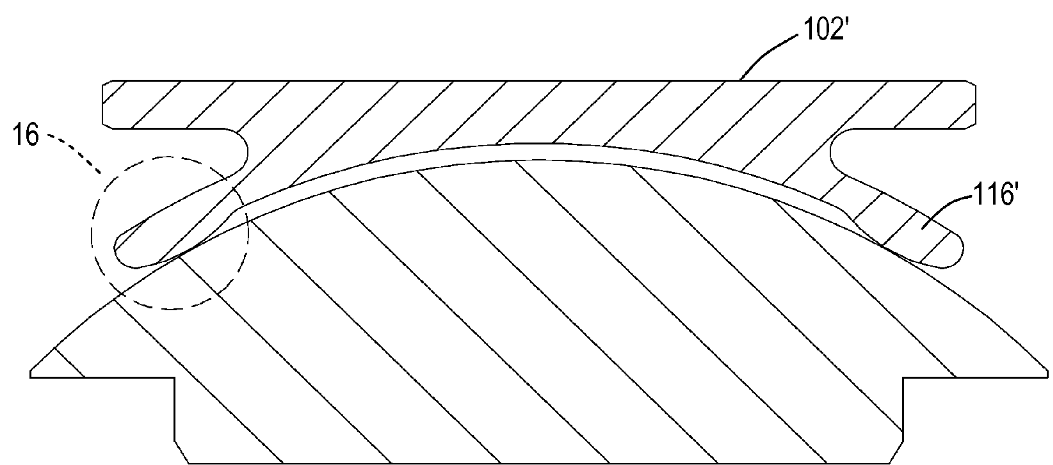
FIG. 15 is a cross-sectional view of an alternative joint member.
Figure 16:
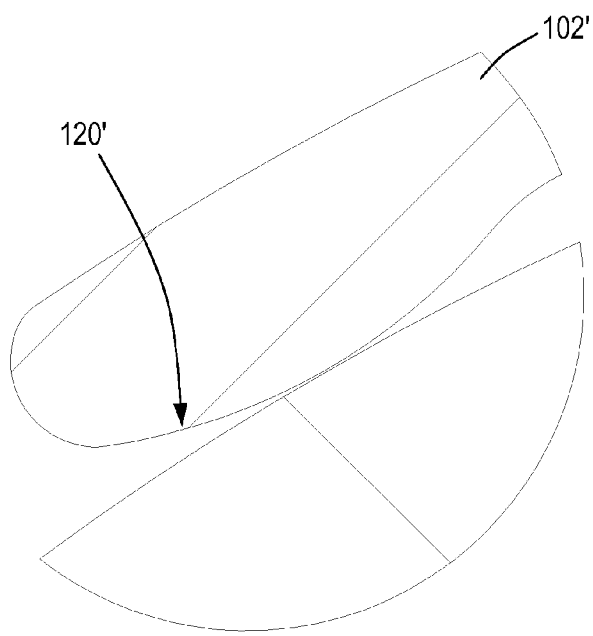
FIG. 16 is an enlarged view of a portion of FIG. 15.

The first contact surface 118 includes a protruding peripheral rim 120 (see FIG. 11), and a recessed central portion 122, which may also be considered a "pocket" or a "relief". As used herein, the term "recessed" as applied to the central portion 122 means that the central portion 122 lies outside of the nominal exterior surface of the second member 104 when the joint 100 is assembled. The terms "recessed" and "protruding" as used herein are opposite in meaning to one another. For example, the peripheral rim 120 protrudes relative to a nominal surface defined by the central portion 122, and the central portion 122 is recessed relative to the rim 120. In one configuration, shown in FIGS. 9-14, and best seen in FIG. 11, the rim 120 is concave, with the radius of curvature being quite high, such that the cross-sectional shape of the surface of the rim 120 approaches a straight line. FIGS. 15 and 16 show another configuration of a joint member 102' with a flange 116' in which the rim 120' has a convex-curved cross-sectional shape. The cross-sectional shape of the rim may be flat or curved as necessary to suit a particular application.

The annular configuration of first contact surface 118 with the protruding rim 120 results in a configuration which permits only pivoting and rotational motion, and is statically and dynamically determinate for the life of the joint 100. In contrast, prior art designs employing mating spherical shapes, even very accurate shapes, quickly reach a statically and dynamically indeterminate condition after use and wear. This condition accelerates wear, contributes to the fretting corrosion wear mechanism, and permits undesired lateral translation between the joint members.

The second member 104 is also made from a rigid material and has a wear-resistant, convex second contact surface 124. The first and second contact surfaces 118 and 124 bear directly against each other so as to transfer axial and lateral loads from one member to the other while allowing pivoting motion between the two members 102 and 104.

Nominally the first and second members 102 and 104 define a "ring" or "band" contact interface therebetween. In practice it is impossible to achieve surface profiles completely free of minor imperfections and variations. If the first and second members 102 and 104 were both completely rigid, this would cause high Hertzian contact stresses and rapid wear. Accordingly, an important feature of the illustrated joint 100 is that the flange 116 (and thus the first contact surface 118) of the first member 102 is conformable to the second contact surface 124 when the joint is placed under load.

Figure 12:
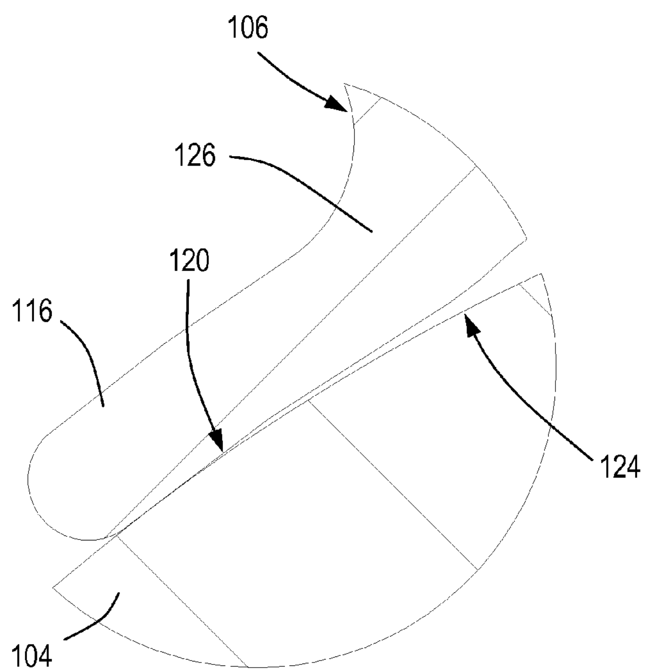
FIG. 12 is an enlarged view of a portion of FIG. 10.
Figure 13:
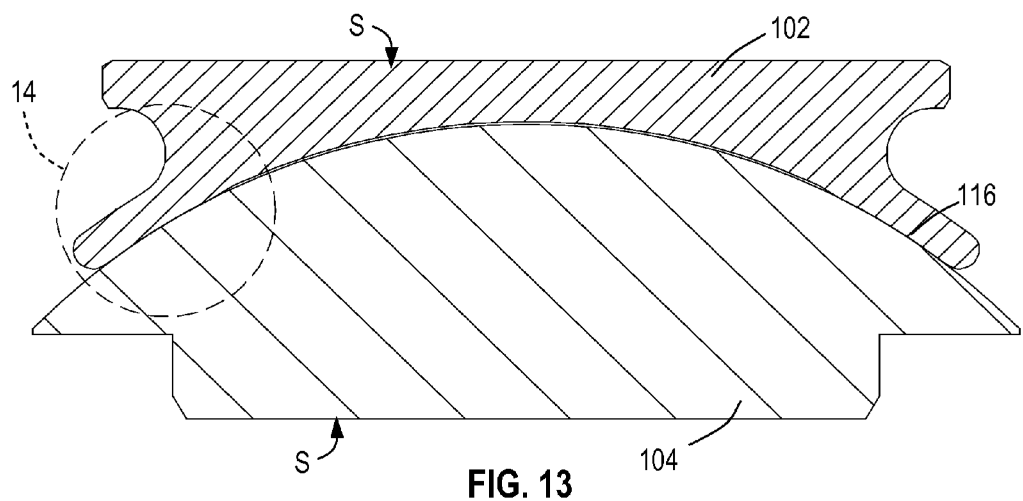
FIG. 13 is a cross-sectional view of the prosthetic joint of FIG. 9 in a loaded condition.

FIGS. 10 and 12 show a cross-sectional view of the flange 116 in an unloaded condition or free shape. It can be seen that the distal end of the rim 120 contacts the second contact surface 124, while the inboard end of the rim 120 (i.e. near where the flange 116 joins the body 106) does not. FIGS. 13 and 14 show the flange 116 in a deflected position or loaded shape, where substantially the entire section width of the rim 120 contacts the second contact surface 124, resulting in a substantially increased contact surface area between the two members 102 and 104, relative to the free shape. The rim 120' of the joint member 102' (see FIG. 16) is similarly conformable; however, given the curved cross-sectional shape, the total amount of surface contact area remains substantially constant in both loaded and unloaded conditions, with the rim 120' undergoing a "rolling" or "rocking" motion as the loading changes.

The conformable nature of the flange 116 is explained in more detail with reference to FIGS. 24 through 30. As noted above, the first member 102 has a flange 116 and a concave first contact surface 118. The second member 104 has a convex second contact surface 124. When assembled and in use the joint 100 is subject, among other loads, to axial loading in the direction of the arrows labeled "F" in FIG. 24 (i.e. along axis "A" of FIG. 10). As previously stated, it is impossible in practice for either of the contact surfaces 118 or 124 to be perfect surfaces (i.e. a perfect sphere or other curve or collection of curves). It is believed that in most cases that a defect such as a protrusion from the nominal contact surface of just 0.00127 mm (0.00005 in.), that is, 50 millionths of an inch, or larger, would be sufficient to cause fretting corrosion and failure of a metal-on-metal joint constructed to prior art standards. A defect may include a variance from a nominal surface shape as well as a discontinuity in the contact surface. Defects may arise through a variety of sources such as manufacturing, installation, and/or operating loads in the implanted joint.

Figure 25:
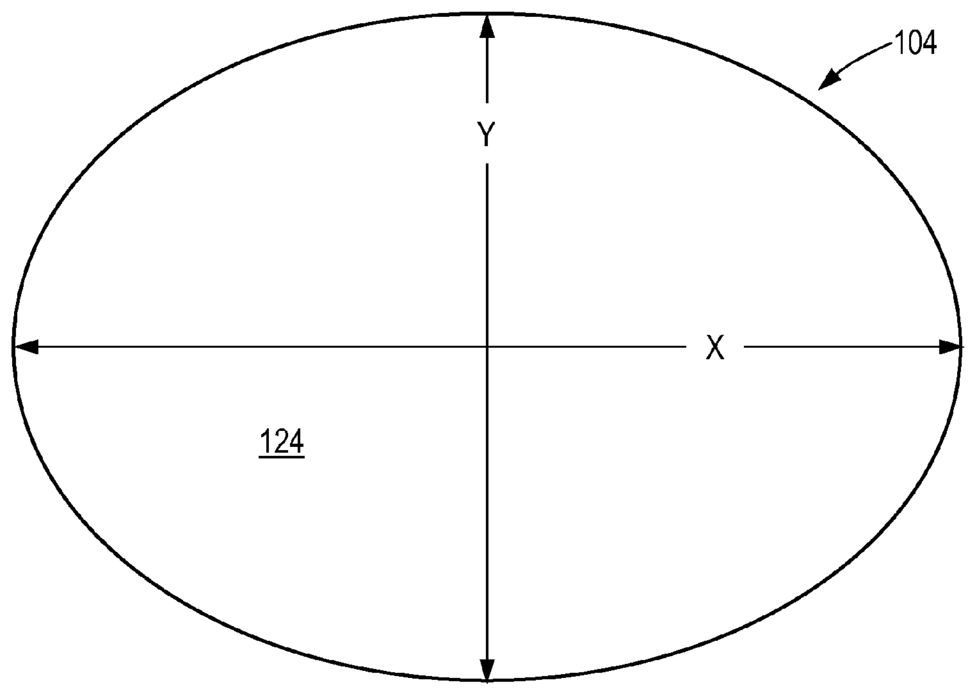
FIG. 25 is a top plan view of one of the joint members shown in FIG. 24.

FIG. 25 shows the second member 104 which in this particular example varies from a nominal shape in that it is elliptical rather than circular in plan view. The elliptical shape is grossly exaggerated for illustrative purposes. For reference, the dimensions of the second member 104 along the major axis labeled "X" is about 0.0064 mm (0.00025 in.) larger than its dimension along the minor axis labeled "Y". When assembled and loaded, the flange 116 conforms to the imperfect second contact surface 124 and deflects in an irregular shape. In other words, in addition to any uniform deflection which may be present, the deflected shape of the flange 116 includes one or more specific locations or portions that are deflected towards or away from the nominal free shape to a greater or lesser degree than the remainder of the flange 116. Most typically the deflected shape would be expected to be non-axisymmetric. For example, the deflection of the flange 116 at points located at approximately the three o'clock and nine o'clock positions is substantially greater than the deflection of the remainder of the flange 116. As a result, the contact stress in that portion of the first contact surface 118 is relieved. FIG. 27 is a plan view plot (the orientation of which is shown by arrow in FIG. 26) which graphically illustrates the expected contact stresses in the first contact surface 118 as determined by analytical methods. The first contour line "C2" shows that a very low level of contract stress is present around the entire perimeter of the first contact surface 118. This is because the entire first contact surface 118 is in contact with the second contact surface 124. Another contour line "C3" represents the areas of maximum contact stress corresponding to the protruding portions of the elliptical second contact surface 124.

Figure 28:
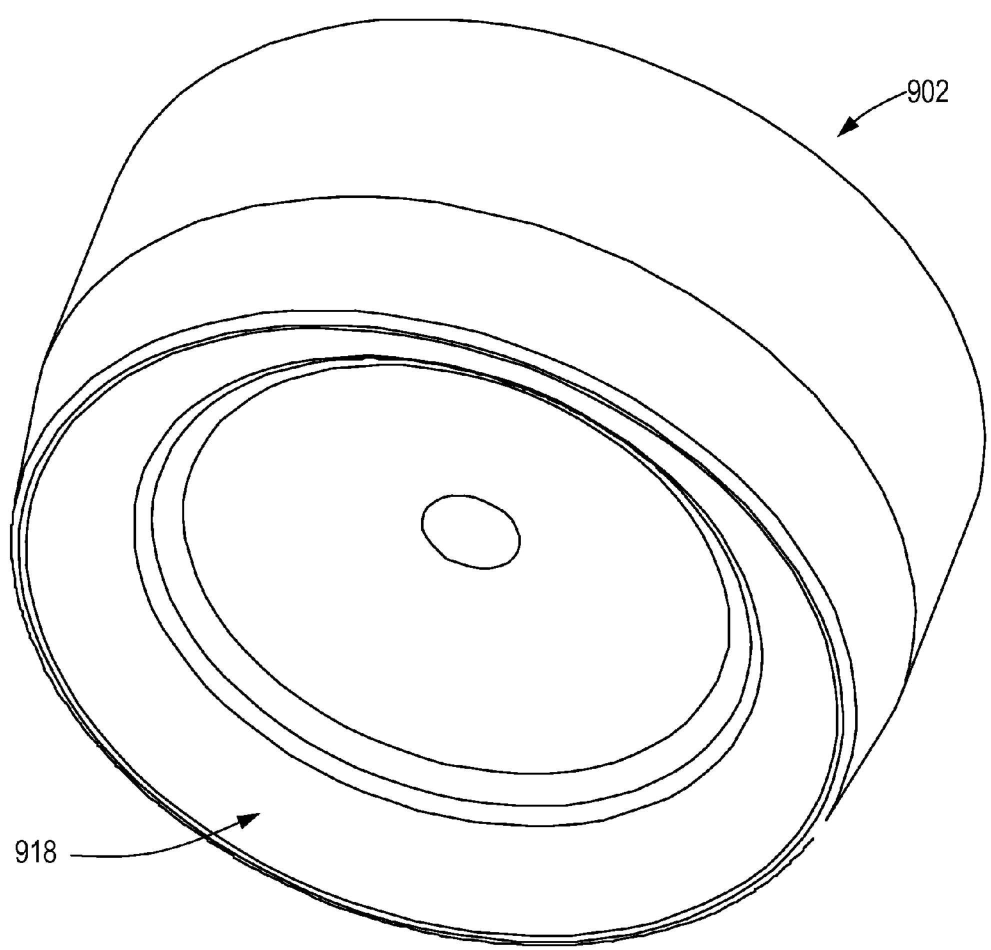
FIG. 28 is a perspective view of a rigid joint member used for comparison purposes.
Figure 29:
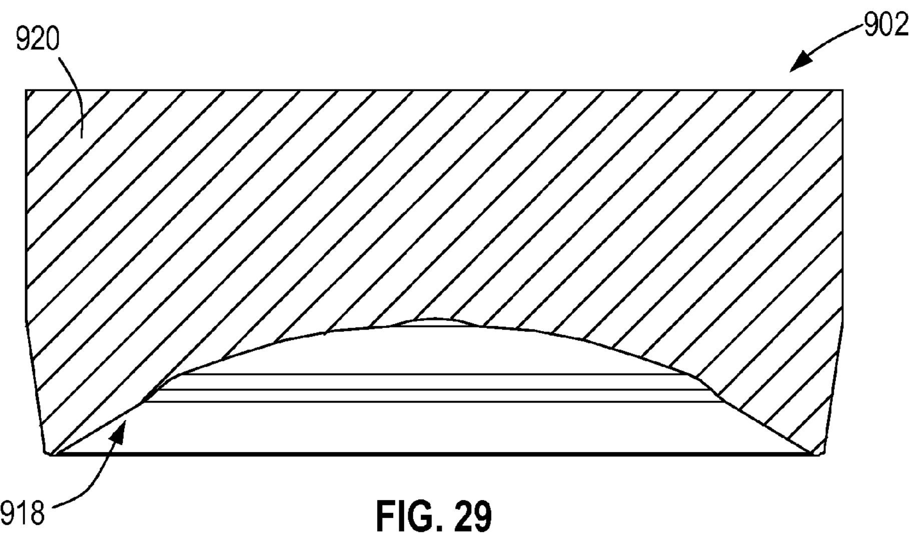
FIG. 29 is a cross-sectional view of the joint member shown in FIG. 28.
Figure 30:
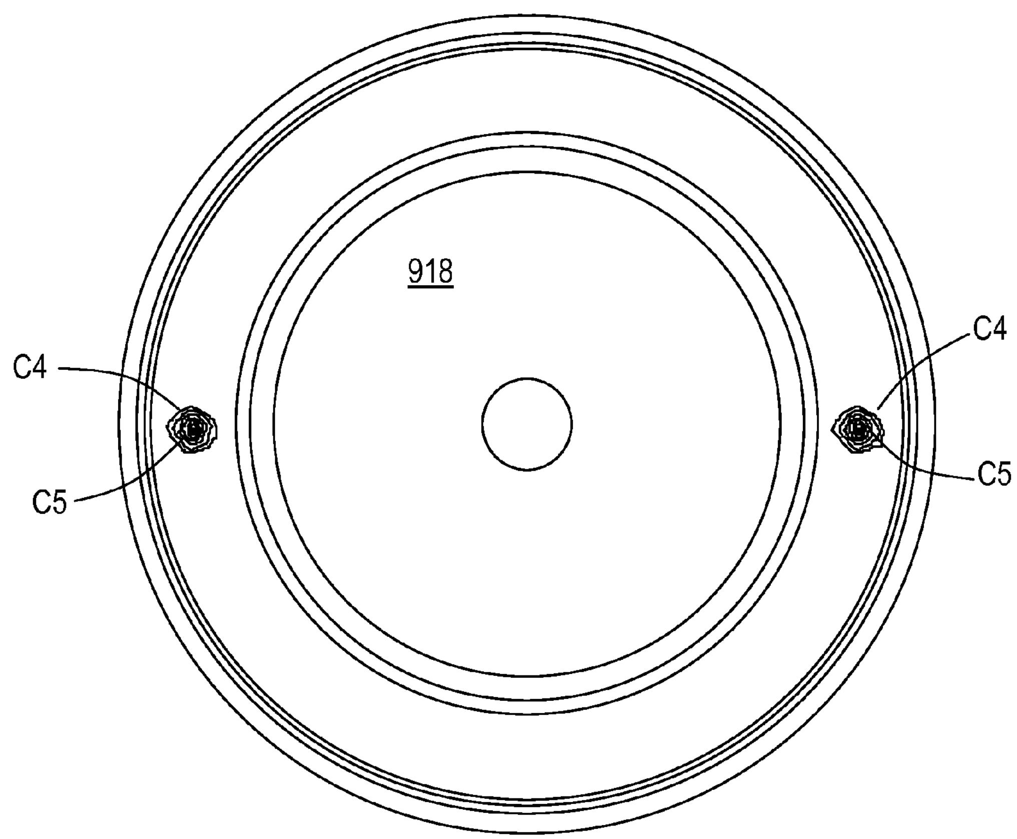
FIG. 30 is a contact stress plot of the joint member shown in FIG. 29.

For comparative purposes, FIGS. 28 and 29 depict a member 902 constructed according to prior art principles. The member 902 has a contact surface 918 with an identical profile and dimensions of the first contact surface 118 of the first member 102. However, consistent with the prior art, the member 902 has a massive body 920 behind the entire contact surface 918, rendering the entire member 902 substantially rigid. FIG. 30 graphically illustrates the expected contact stresses in the contact surface 918 as determined by analytical methods, when the member 902 is assembled and placed in contact with the second member 104, using the same applied load as depicted in FIG. 27. Because of the rigidity of the member 902, a "bridging" effect is present wherein contact between the contact surfaces (one of which is circular in plan view, and the other of which is elliptical) effectively occurs at only two points, located at approximately the three o'clock and nine o'clock positions. A first contour line "C4" shows two discrete areas where the lowest level of contract stress is present. These lines are not contiguous because there is no contact in the remaining area of the contact surfaces (for example at the six o'clock and twelve o'clock positions). Another contour line "C5" represents the areas of maximum contact stress. Analysis shows a peak contact stress having a magnitude of two to twenty times (or more) the peak contact stress of the inventive joint as shown in FIG. 27.

To achieve this controlled deflection, the flange 116 is thin enough to permit bending under working loads, but not so thin as to allow material yield or fatigue cracking The deflection is opposed by the elasticity of the flange 116 in bending, as well as the hoop stresses in the flange 116. To achieve long life, the first member 102 is sized so that stresses in the flange 116 will be less than the endurance limit of the material, when a selected external load is applied. In this particular example, the joint 100 is intended for use between two spinal vertebrae, and the design average axial working load is in the range of about 0 N (0 lbs.) to about 1300 N (300 lbs.). These design working loads are derived from FDA-referenced ASTM and ISO standards for spinal disc prostheses. In this example, the thickness of the flange 116, at a root 126 where it joins the body 106 (see FIG. 12) is about 0.4 mm (0.015 in.) to about 5.1 mm (0.200 in.), where the outside diameter of the flange 116 is about 6.4 mm (0.25 in.) to about 7.6 cm (3.0 in.).

Figure 17:
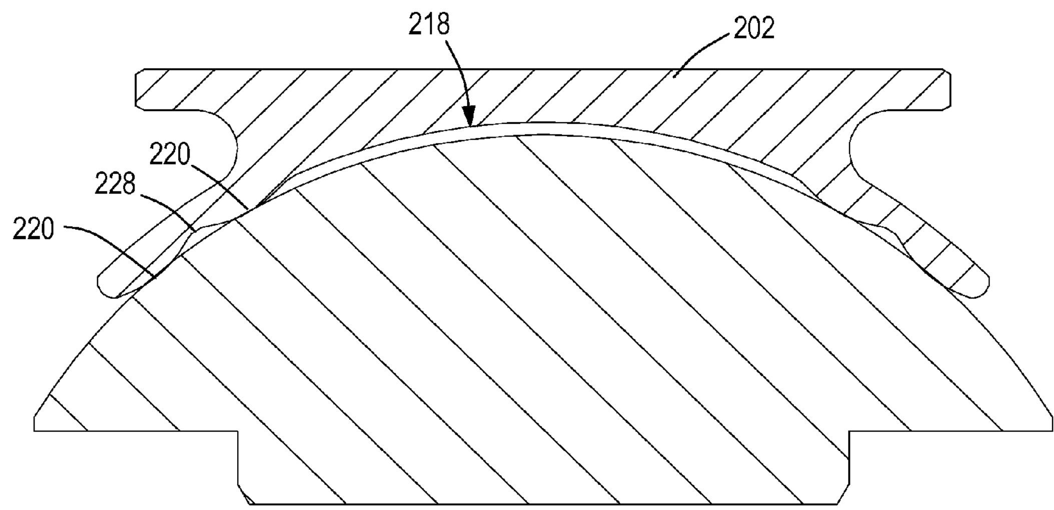
FIG. 17 is a cross-sectional view of another alternative joint member.

The joint members may include multiple rims. For example, FIG. 17 illustrates a joint member 202 where the first contact surface 218 includes two protruding rims 220, with a circumferential groove or relief area 228 therebetween. The presence of multiple rims increases the contact surface areas between the two joint members.

Figure 18:
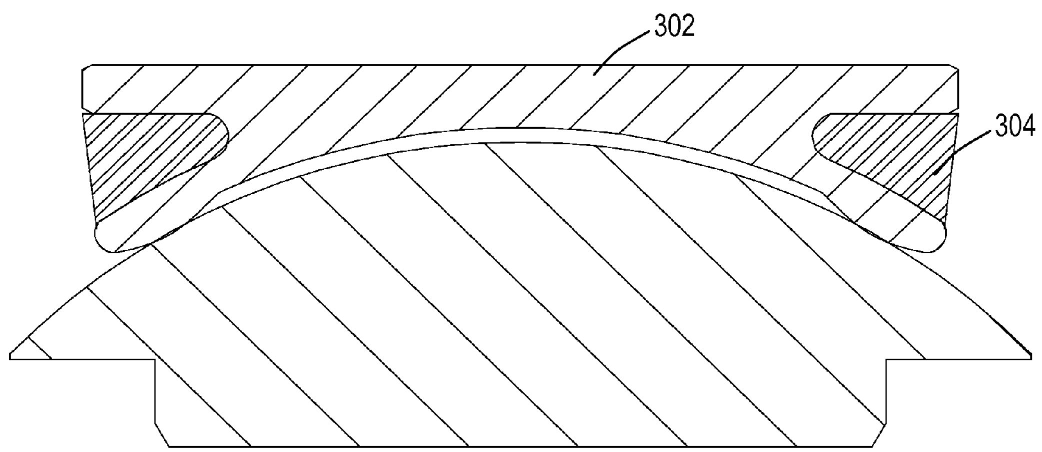
FIG. 18 is a cross-sectional view of another alternative joint member including a filler material.

If present, the circumferential gap between the flange and the base of the joint member may be filled with resilient nonmetallic material to provide damping and/or additional spring restoring force to the flange. FIG. 18 illustrates a joint member 302 with a filler 304 of this type. Examples of suitable resilient materials include polymers, natural or synthetic rubbers, and the like.

Figure 19:
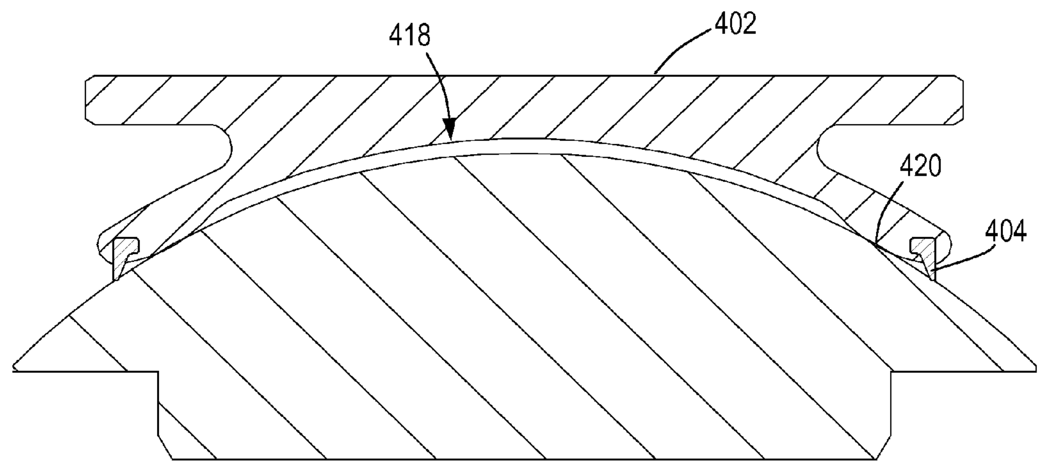
FIG. 19 is a cross-sectional view of another alternative joint member including a wiper seal.

As discussed above, the joint may incorporate a wiper seal. For example, FIG. 19 illustrates a joint member 402 with a resilient wiper seal 404 protruding from the rim 420 of the first contact surface 418. The wiper seal 404 keeps particles out of the contact area (seal void), while containing working fluid (natural or synthetic). The seal geometry is intended to be representative and a variety of seal characteristics may be employed; such as a single lip seal, a double or multiple lip seal. A pad or wiper seal may be made from a variety of material options. Different seal mounting options may be used, for example a lobe in shaped groove as shown in FIG. 18, a retaining ring or clamp, adhesion substance. The seal may also be incorporated into the contact face of the interface zone.

Figure 20:
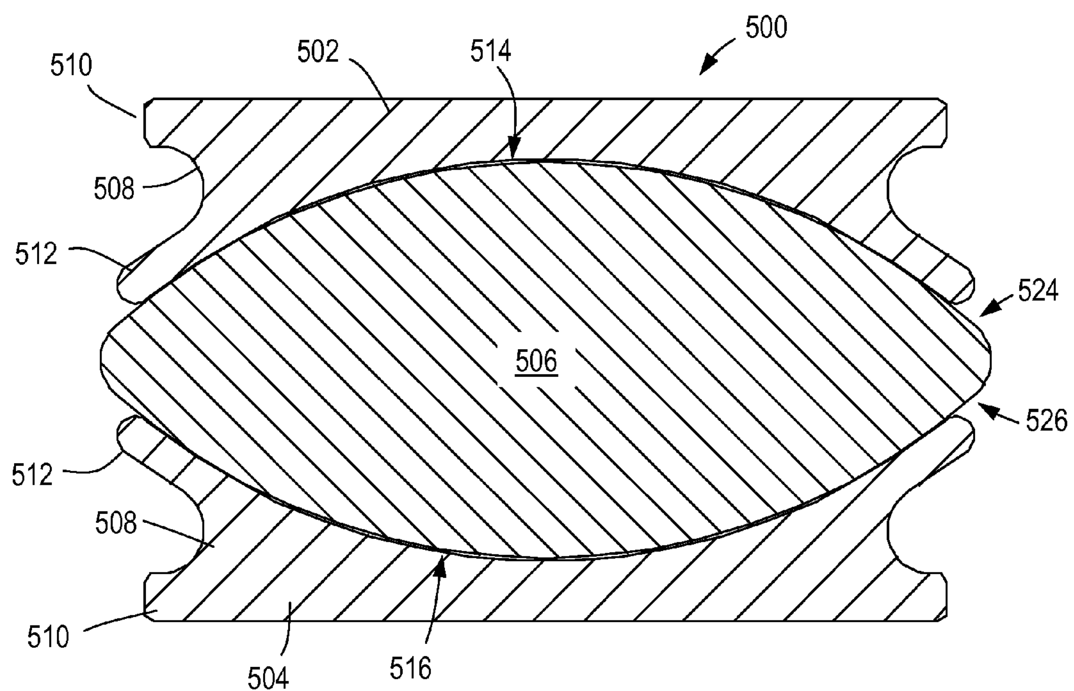
FIG. 20 is a cross-sectional view of another alternative prosthetic joint.

The joint construction described above can be extended into a three-part configuration. For example, FIG. 20 illustrates a prosthetic joint 500 having first, second, and third members 502, 504, and 506. The first and second members 502 and 504 are similar in construction to the first member 102 described above, and each includes a body 508, an optional disk-like base 510, and a flange 512. The flanges 512 define wear-resistant concave first and second contact surfaces 514 and 516, each of which includes a protruding peripheral rim, and a recessed central portion as described above. The third member 506 has a double-convex shape defining opposed wear-resistant, convex third and fourth contact surfaces 524 and 526. The first and second 514 and 516 bear against the third and fourth contact surfaces 524 and 526, respectively, so as to transfer axial (i.e. compression) and lateral loads between the first and second members 502 and 504 through the third member 506, while allowing pivoting motion between the members 502, 504, and 506. The first and second contact surfaces 514 and 516 are conformal to the third and fourth contact surfaces 524 and 526 as described in more detail above.

Figure 21:
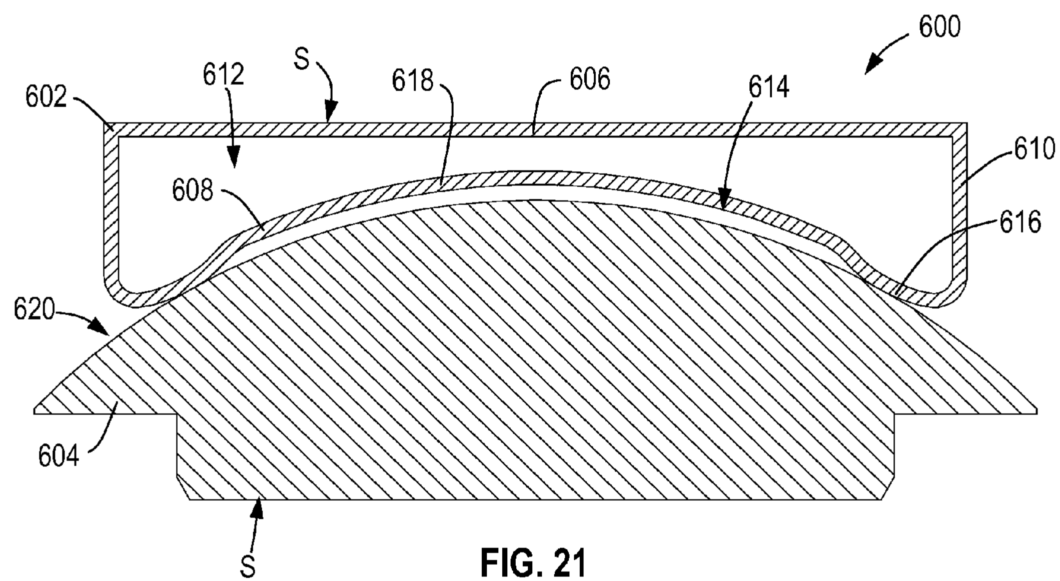
FIG. 21 is a cross-sectional view of a prosthetic joint constructed in accordance with another aspect of the present invention.

FIG. 21 illustrates an alternative prosthetic joint 600 comprising first and second members 602 and 604 constructed from rigid materials. Both of the members 602 and 604 may be bone-implantable, meaning they include osseointegration surfaces, labeled "S", as described in more detail above.

The first member 602 is hollow and includes a disk-like base 606 and a cup 608, interconnected by a peripheral wall 610. An interior cavity 612 is defined between the base 606 and the cup 608. The cup 608 is constructed from a rigid material and defines a wear-resistant, concave first contact surface 614. The first contact surface 614 includes a protruding peripheral rim 616, and a recessed central portion 618, which may also be considered a "pocket" or a "relief". The rim 616 may have a conical or curved cross-sectional shape. The interior cavity 612 may be filled with resilient nonmetallic material to provide damping and/or additional spring restoring force to the flange. Examples of suitable resilient materials include polymers, natural or synthetic rubbers, and the like.

The second member 604 is constructed from a rigid material and has a wear-resistant, convex second contact surface 620. The first and second contact surfaces 614 and 616 bear directly against each other so as to transfer axial and lateral loads from one member to the other while allowing pivoting motion between the two members 602 and 604.

As described above with reference to the prosthetic joint 100, the cup 606 of the first member 602 is thin enough to permit bending under working loads, but not so thin as to allow material yield or fatigue cracking. The first contact surface 614 is thus conformable to the second contact surface 620 when the prosthetic joint 600 is placed under external load.

Figure 22:
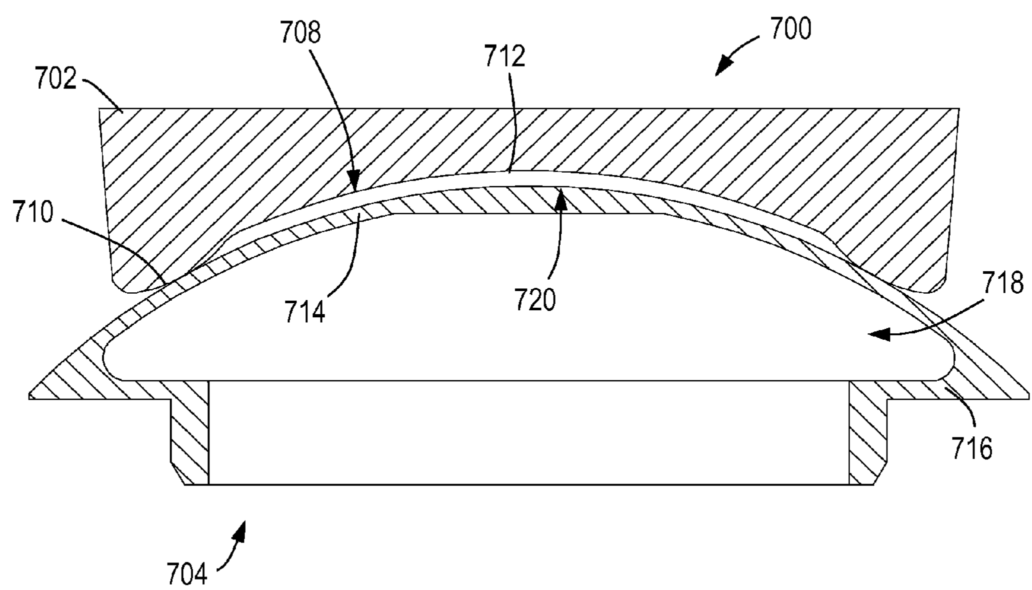
FIG. 22 is a cross-sectional view of a prosthetic joint constructed in accordance with yet another aspect of the present invention.

An inverted configuration of hollow members is also possible. For example, FIG. 22 illustrates a prosthetic joint 700 comprising first and second members 702 and 704, both constructed of rigid materials. The first member 702 is solid and includes a wear-resistant, concave first contact surface 708. The first contact surface 708 includes a protruding peripheral rim 710, and a recessed central portion 712, which may also be considered a "pocket" or a "relief".

The second member 704 is hollow and includes a dome 714 connected to a peripheral wall 716. An interior cavity 718 is defined behind the dome 714. The dome 714 defines a wear-resistant, convex second contact surface 720, which is shaped and sized enough to permit bending under working loads, but not so as to allow material yield or fatigue cracking The second contact surface 720 is thus conformable to the first contact surface 708 when the prosthetic joint 700 is placed under external load.

The first and second contact surfaces 708 and 720 bear directly against each other so as to transfer axial and lateral loads from one member to the other while allowing pivoting motion between the two members 702 and 704.

Figure 23:
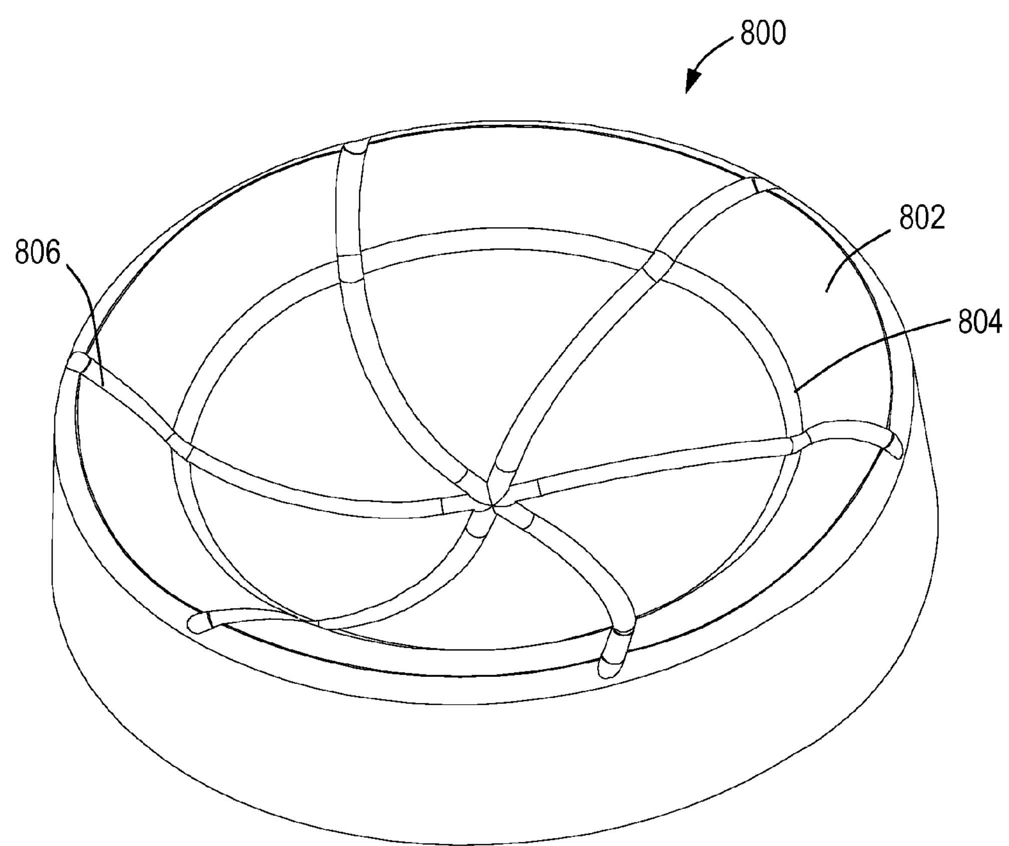
FIG. 23 is a perspective view of a joint member having a grooved surface.
Figure 24:
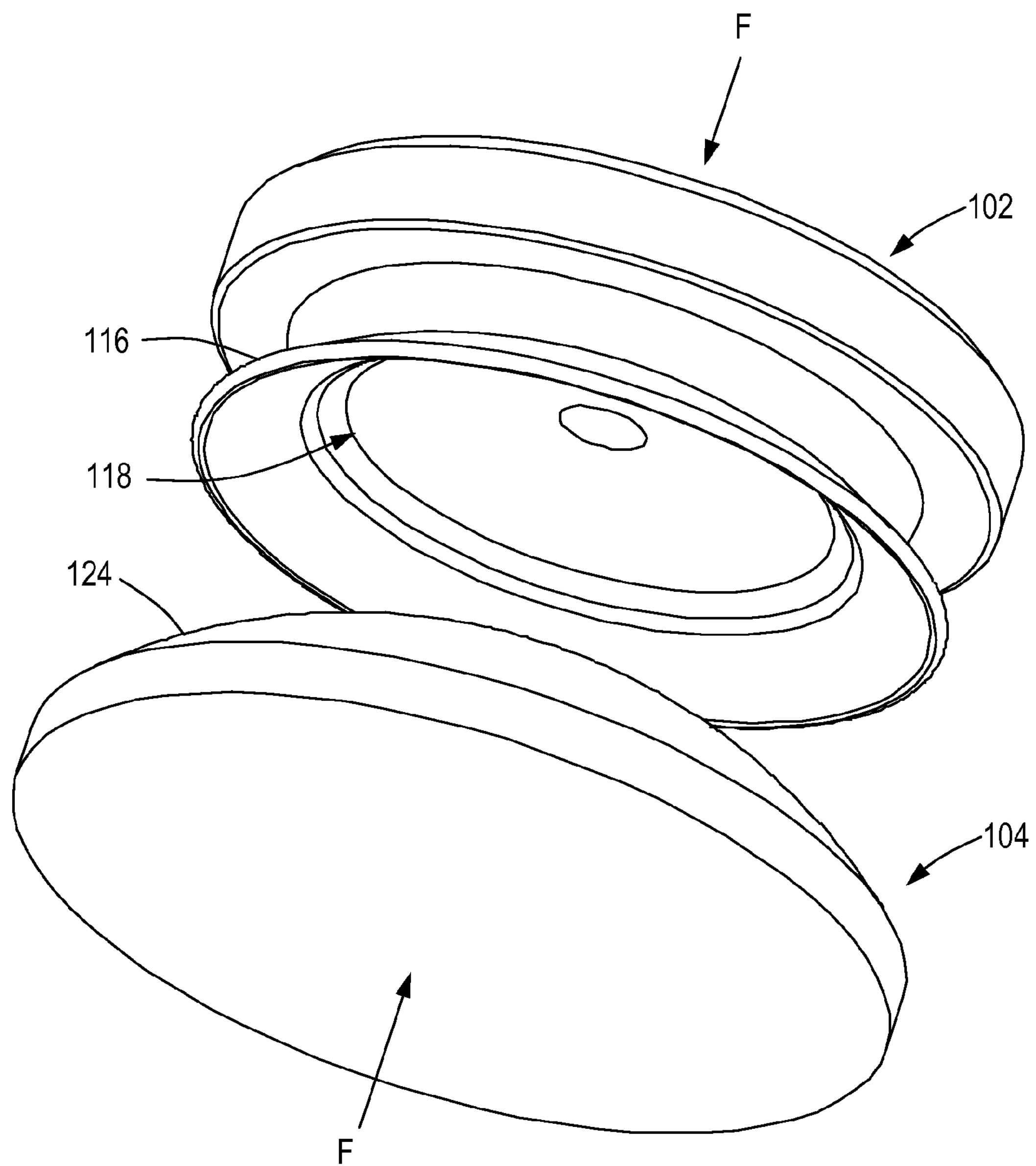
FIG. 24 is a exploded perspective view of two mating joint members.

Any of the contact surfaces described above may be provided with one or more grooves formed therein to facilitate flow of fluid or debris. For example, FIG. 23 illustrates a joint member 800 including a concave contact surface 802. The contact surface 802 includes a circular groove 804, and plurality of generally radially-extending grooves 806 which terminate at the center of the contact surface 802 and intersect the circular groove 804.

Figure 31:
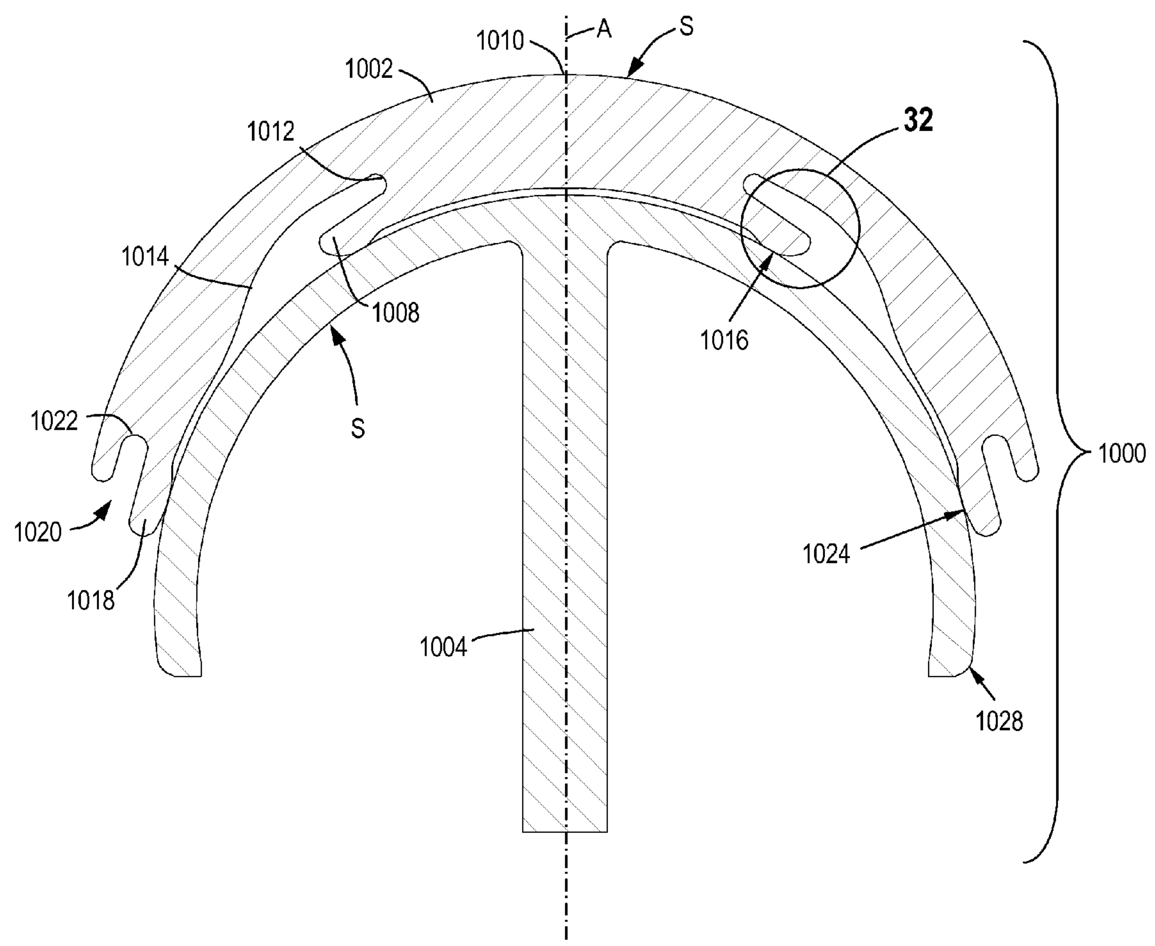
FIG. 31 is a cross-sectional view of a prosthetic joint constructed in accordance with another aspect of the present invention.
Figure 32:
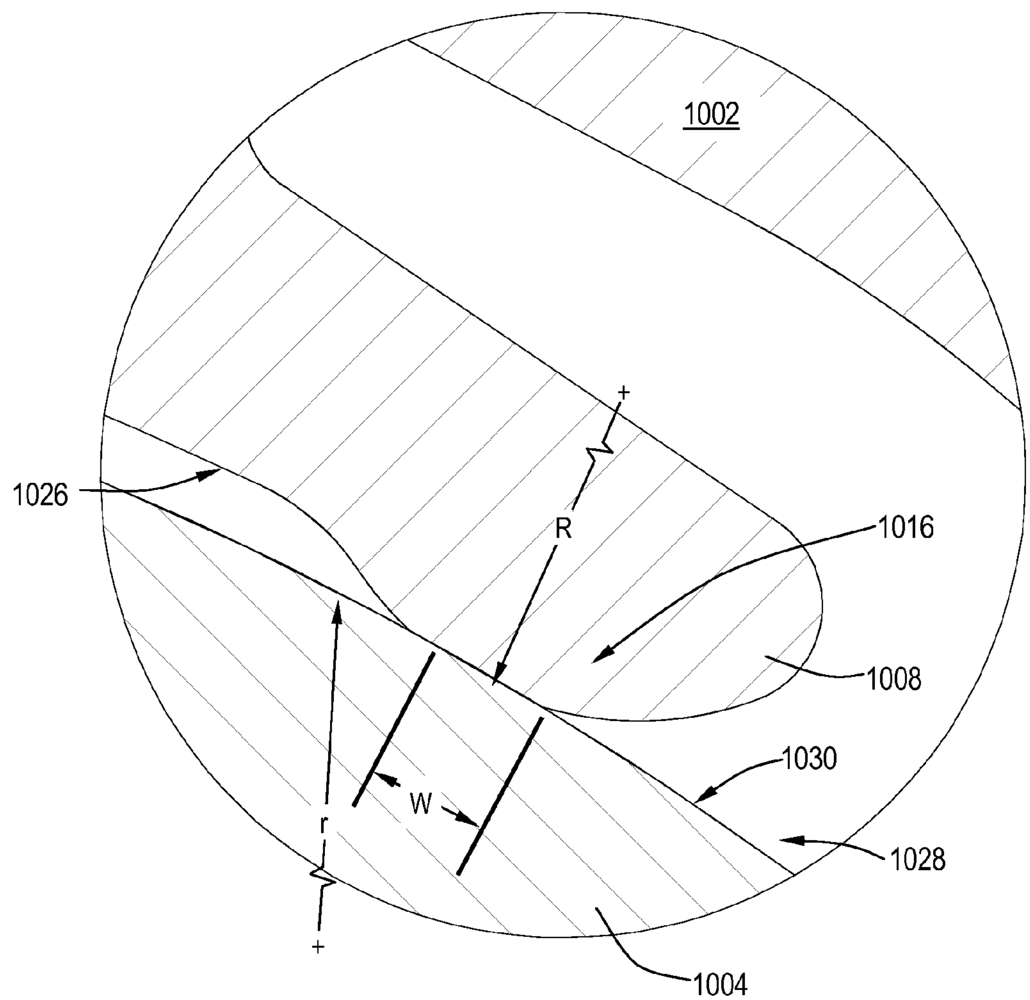
FIG. 32 is an enlarged view of a portion of the joint shown in FIG. 31.
Figure 33:
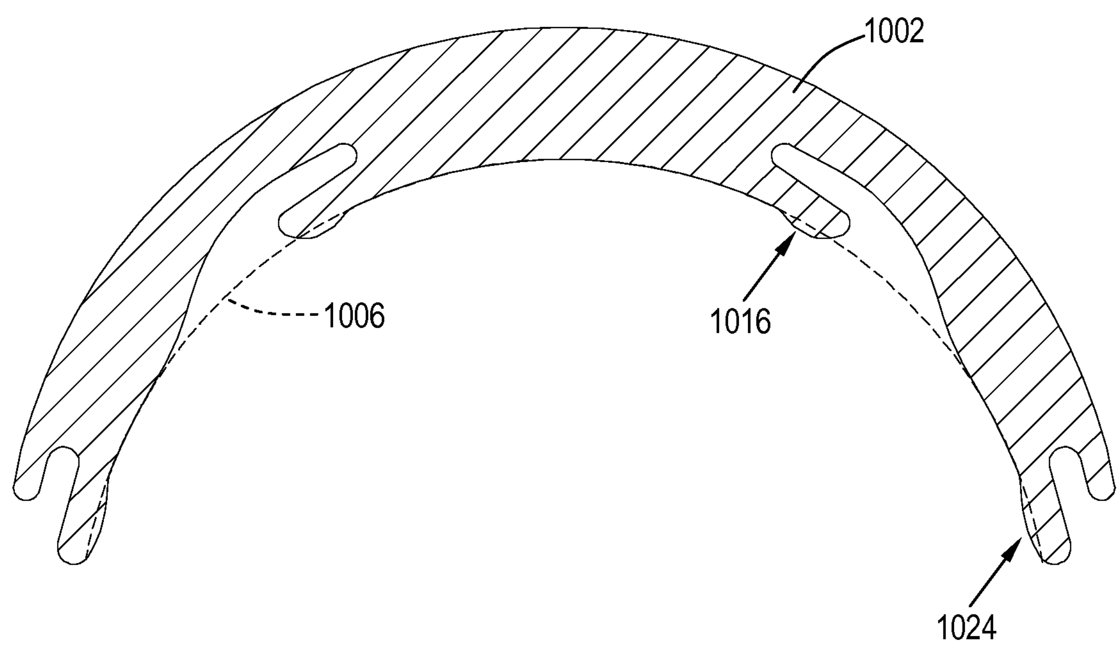
FIG. 33 is a cross-sectional view of a cup member of the joint shown in FIG. 31.

FIGS. 31-33 illustrate an alternative prosthetic joint 1000 comprising first and second members 1002 and 1004. The illustrated prosthetic joint 1000 is particularly adapted for a ball-and-socket joint application such as is found in a human hip joint (i.e. the acetabulofemoral joint) or shoulder joint (i.e. the glenohumeral joint), but it will be understood that the principles described herein may be applied to any type of prosthetic joint. Both of the members 1002 and 1004 may be bone-implantable, meaning they include osseointegration surfaces, labeled "S", which are surfaces designed to be infiltrated by bone growth to improve the connection between the implant and the bone. Osseointegration surfaces may be made from materials such as TRABECULAR METAL, textured metal, or sintered or extruded implant integration textures, as described above. As shown in FIG. 31, a nominal central axis "A" passes through the centers of the first and second members 1002 and 1004 In the illustrated examples, the first and second joint members 1002 and 1004 are bodies of revolution about this axis, but the principles of the present invention also extend to non-axisymmetric shapes.

The first member 1002 is constructed from a rigid material as described above. The first member 1002 is concave and may generally be thought of as a "cup", although it need not have any particular degree of curvature. Its interior defines a cup surface 1006 with a nominal profile shown by the dashed line in FIG. 33. The interior includes an annular first flange 1008 which is located relatively near an apex 1010 of the first member 1002 and which extends in a generally radial direction relative to the axis A. The first flange 1008 is defined in part by an undercut groove 1012 formed in the first member 1002. A ramped surface 1014 forms a transition from the groove 1012 to the nominal cup surface 1006. The first flange 1008 includes a protruding first contact rim 1016. As used herein, the term "protruding" as applied to the first contact rim 1016 means that the first contact rim 1016 lies inside of the nominal profile of the cup surface 1006 when the joint 1000 is assembled. The first contact rim 1016 may have a curved or toroidal cross-sectional shape.

The interior also includes an annular second flange 1018 which is located at or near an outer peripheral edge 1020 of the first member 1002 and which extends in a generally axial direction relative to the axis A. The second flange 1018 is defined in part by an undercut groove 1022 formed in the first member 1002. The second flange 1018 includes a protruding second contact rim 1024. As used herein, the term "protruding" as applied to the second contact rim 1024 means that the second contact rim 1024 lies inside of the nominal cup surface 1006 when the joint 1000 is assembled. The second contact rim 1024 may have a curved or toroidal cross-sectional shape. Depending on the particular application, joint 1000 may include more than two flanges defining more than two contact rims.

In the illustrated example, the first member 1002 includes a face layer 1026 of a known coating such as titanium nitride, chrome plating, carbon thin films, and/or diamond-like carbon coatings, and/or a another substantially thicker wear-resistant material such as ultra-high molecular weight (UHMW) polyethylene. This face layer 1026 is used to impart wear resistance, as described above. The face layer 1026 may be extraordinarily thin. In this particular example, its as-applied thickness is about 0.0041 mm (0.00016 in.), or 160 millionths of an inch thick. The face layer 1026 is applied at a substantially uniform thickness over the surface profile which is defined by machined or formed features of the substrate. Alternatively, and especially if a much thicker face layer were used, the face layer could be profiled so as to define both the nominal cup surface 1006 and the first and second contact rims 1016 and 1024.

The second member 1004 is also made from a rigid material and has a wear-resistant, convex contact surface 1028. In the specific example illustrated, the second member 1004 includes a face layer 1030 of a known coating such as titanium nitride, chrome plating, carbon thin films, and/or diamond-like carbon coatings, and/or a another substantially thicker wear-resistant material such as ultra-high molecular weight (UHMW) polyethylene. This face layer 1030 is used to impart wear resistance, and may be quite thin, as described above. The first and second contact rims 1016 and 1024 bear directly against the contact surface 1028 so as to transfer axial and lateral loads from one member to the other while allowing pivoting motion between the two members 1002 and 1004.

The annular configuration of contact rims 1016 and 1024 results in a joint configuration which permits only pivoting and rotational motion, and is statically and dynamically determinate for the life of the joint 1000. In particular, the presence of the relatively widely-spaced contact rims 1016 and 1024, and the peripheral positioning of the second contact rim 1024 is highly effective in resisting any translation of the first and second members 1002 and 1004 lateral to the axis A.

Nominally the first and second contact rims 1016 and 1024 define two separate "ring" or "band" contact interfaces with the contact surface 1028 of the second member 1004. In practice it is impossible to achieve surface profiles completely free of minor imperfections and variations. If the first and second members 1002 and 1004 were both completely rigid, this would cause high Hertzian contact stresses (i.e. non-uniform contact) and rapid wear. Accordingly, an important feature of the illustrated joint 1000 is that the flanges 1008 and 1018 (and thus the contact rims 1016 and 1024) of the first member 1002 are conformable to the contact surface 1028 when the joint 1000 is placed under load. The flanges 1008 and 1018 can conform to the imperfect contact surface 1028 and deflect in an irregular shape. In other words, in addition to any uniform deflection which may be present, the deflected shape of the flanges 1008 and 1018 can include one or more specific locations or portions that are deflected towards or away from the nominal free shape to a greater or lesser degree than the remainder of the flanges 1008 and 1018. To achieve this controlled deflection, the flanges 1008 and 1018 are thin enough to permit bending under working loads, but not so thin as to allow material yield or fatigue cracking, or to exceed the endurance limit of the material. The deflection is opposed by the elasticity of the flanges 1008 and 1018 in bending, as well as the hoop stresses in the flanges 1008 and 1018.

Figure 36:
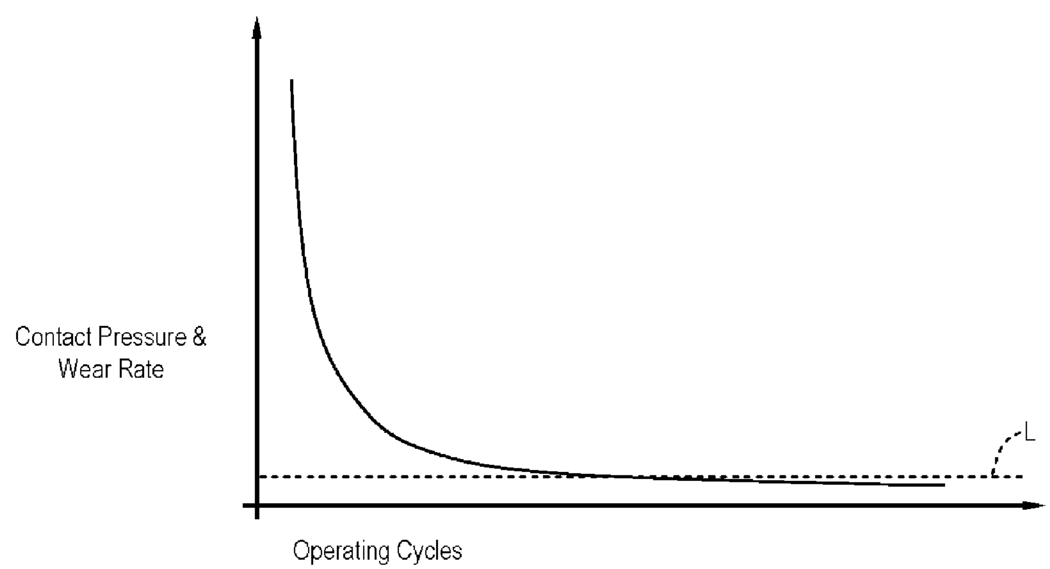
FIG. 36 is a graph showing contact pressure of the joint of FIG. 31 compared to the number of operating cycles.

The contact rims 1016 and 1024 are designed in conjunction with the contact surface 1028 to create a wear characteristic that is constantly diminishing (similar to an asymptotic characteristic). With reference to FIG. 32, the as-manufactured or initial curvatures (e.g. radii) of the first and second contact rims 1016 and 1024, denoted "R" are different from the curvature (e.g. radius) of the contact surface 1028, denoted "r". It is noted that the direction of curvature (i.e. the convexity or second derivative shape) of the first and second contact rims 1016 and 1024 may be the same as, or opposite to, that of the contact surface 1028 upon initial manufacture. In this example they are opposite. When assembled and placed under load, the annular interface between each of the contact rims 1016 and 1024 and the contact surface 1028 will have a characteristic width denoted "W", (effectively creating a contact band). The initial dimensions R and r are selected such that, even using highly wear-resistant surfaces or coatings, some wear takes place during an initial wear-in period of movement cycles. As a result, the contact band width W increases during the initial wear-in period. This increases contact area and therefore decreases contact stress for a given load. After the initial wear-in period (which preferably occurs before the joint is implanted), the contact band reaches a post wear-in width at which the contact stress is below a selected limit, below which the rate of wear in the contacting surfaces approaches a very low number or zero, consistent with a long life of the joint 1000. FIG. 36 illustrates this wear characteristic, with the limit "L" depicted as a horizontal line.

Figure 34:
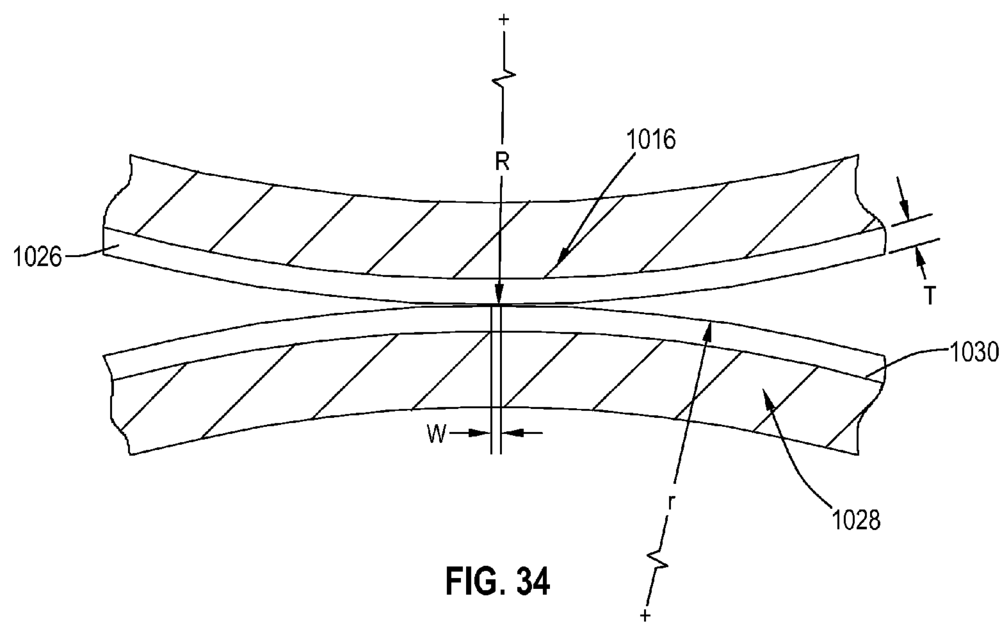
FIG. 34 is a greatly enlarged cross-sectional view of a portion of the joint shown in FIG. 31 in an initial condition.
Figure 35:
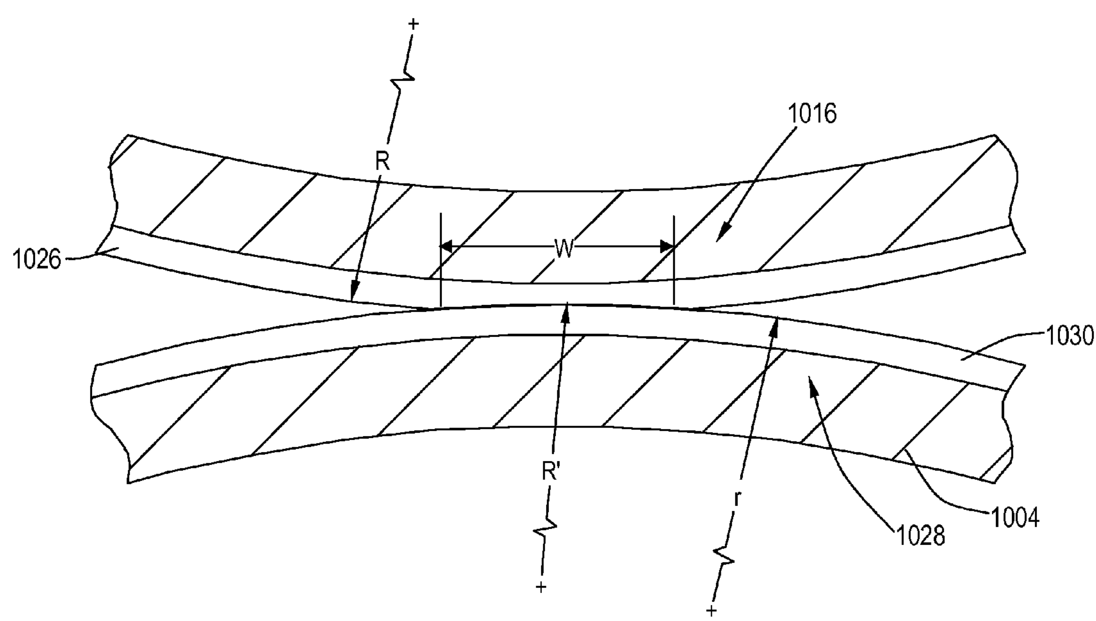
FIG. 35 is a greatly enlarged cross-sectional view of a portion of the joint shown in FIG. 31 after an initial wear-in period.

FIGS. 34 and 35 are schematic views showing the initial wear-in of the surface of the contact rim 1016 at a microscopic (or nearly microscopic) level. It will be understood that these figures are greatly exaggerated for the purposes of illustration. On initial manufacture, as shown in FIG. 34, the curvatures R and r of the contact rim 1016 and the contact surface 1028 have opposite directions. When assembled, the contact band width W is some nominal value, for example about 0.03 mm (0.001 in.), and the total thickness "T" of the face layer 1026 is at its as-applied value of about 0.0041 mm (0.00016 in.) for example. The action of the wear-in period described causes the face layer 1026 to wear to a shape complementary to the contact surface 1028. After this wear-in period the curvature of the portion of the contact rim 1016 within the contact band, denoted "R'", and the curvature r of the contact surface 1028 are in the same direction, and the values of the two curvatures are substantially the same. For example, the thickness T at the location of the contact band may decrease by about 0.0004 mm (0.000014 in.), with a corresponding increase in the width of the contact band W to about 0.2 mm (0.008 in.). Analysis shows that this increase in contact band width and surface area can reduce mean contact pressure by over 80%.

The configuration of the flanges 1008 and 1018 are important in developing the constantly diminishing wear characteristics described above. In particular, the flanges 1008 and 1018 are sized and shaped so that deflections of the contact rims 1016 and 1024 under varying load are always essentially normal to their respective tangent points on the opposing contact surface 1028, as the joint 1000 is loaded and unloaded. This ensures that the position of each of the contact bands remains constant and that the contact bands remain substantially uniform around the entire periphery of the joint 1000.

Figure 37:
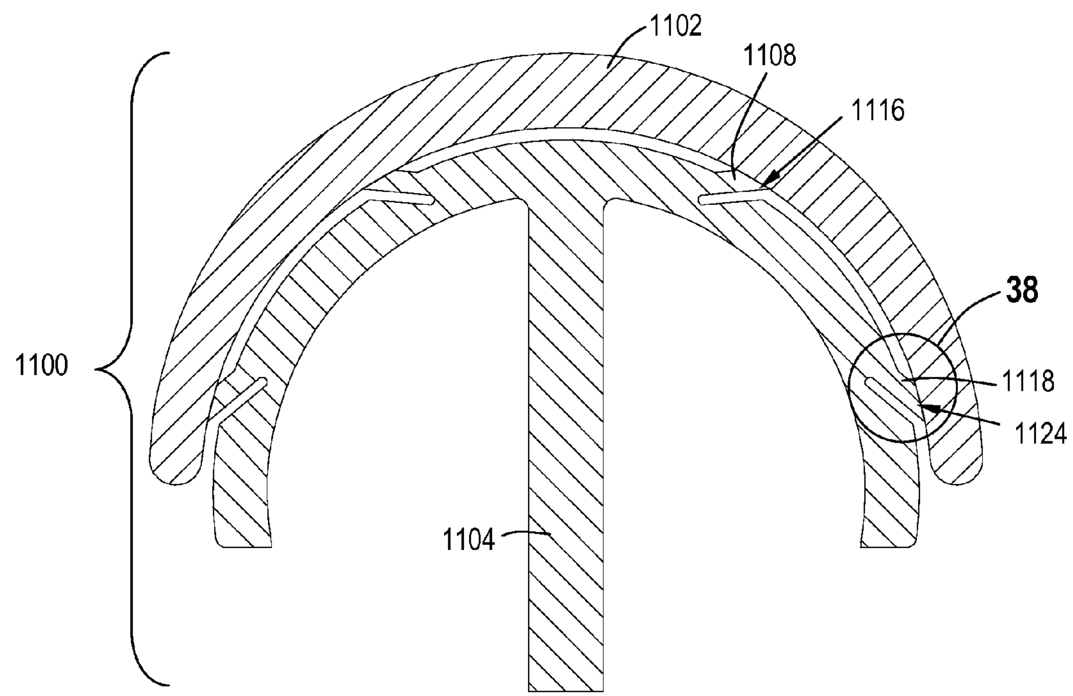
FIG. 37 is a cross-sectional view of a prosthetic joint constructed in accordance with another aspect of the present invention.
Figure 38:
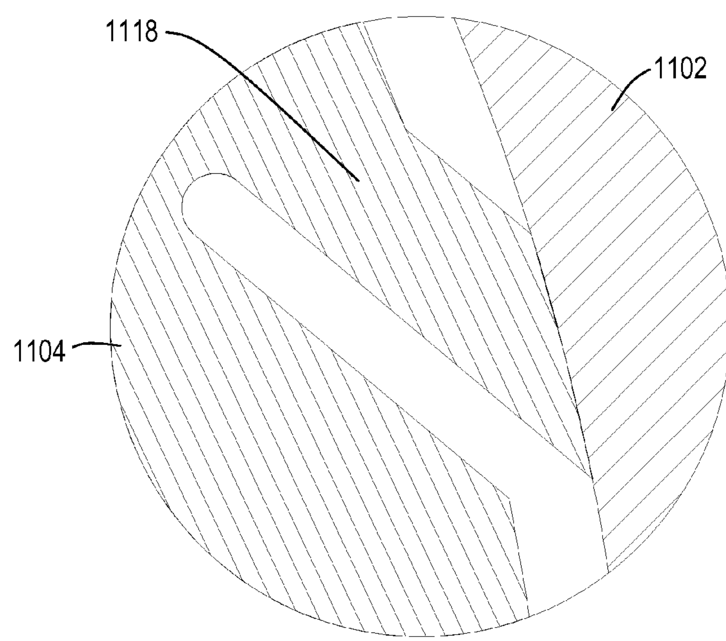
FIG. 38 is an enlarged view of a portion of the joint shown in FIG. 37

An inverted configuration of the joint described above may be used. For example, FIGS. 37 and 38 illustrate a prosthetic joint 1100 having first and second members 1102 and 1104 which are substantially similar in general construction to the members of the joint 1000 described above in terms of materials, coatings, and so for forth. However, in this joint 1100, the concave member 1102 has a contact surface without protruding rings. The convex member 1104 has first and second flanges 1108 and 1118 which define first and second contact rims 1116 and 1124 which function in the same manner that the flanges and contact rims described above.

Figure 39:
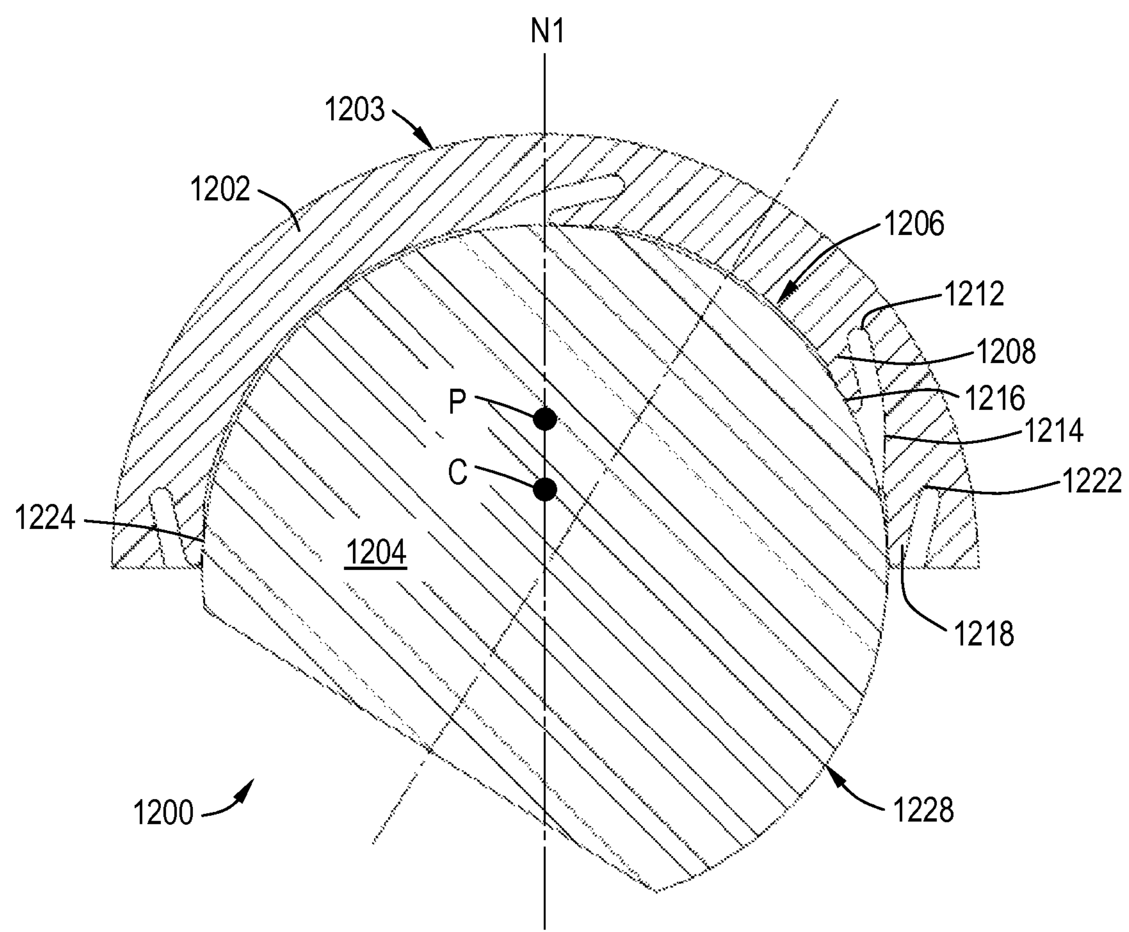
FIG. 39 is a cross-sectional view of a prosthetic joint constructed in accordance with another aspect of the present invention.

FIG. 39 illustrates an alternative prosthetic joint 1200 comprising first and second members 1202 and 1204. The illustrated prosthetic joint 1200 is generally similar in construction and function to the prosthetic joint 1000 described above, and one or both of the members 1202 and 1204 may be bone-implantable as described above.

For purposes of explanation and illustration the first member 1202 will be described relative to a "balanced centroidal axis", labeled "N1" in FIG. 39, passing through it. As used herein, the term "balanced centroidal axis" refers to a virtual line, parallel to local gravity (i.e. a local vertical), which passes through the geometric centroid of the first member 1202, labeled "C", when the first member is in a balanced position (i.e. when there is no rotation of the first member due to unbalanced mass). It is noted that, where the first member 1202 is presumed to have a uniform density, the centroid C will be co-located with its center of mass. If the first member 1202 were suspended in a balanced condition by a point "P" vertically above the centroid C, the balanced centroidal axis N1 would coincide with a local vertical axis passing through the centroid C. In the case where the first member 1202 is a body of revolution, the balanced centroidal axis N1 would coincide or nearly coincide with the generating axis of the first member 1202.

The first member 1202 is constructed from a rigid material and may generally be thought of as a "cup", as described above. Its interior defines a wear-resistant cup surface 1206 including a nominal profile. The interior includes a cantilevered first flange 1208, defined in part by an undercut groove 1212 formed in the first member 1202. Without regard to the exact direction that the flange 1208 extends, it may be considered to be cantilevered relative to the remainder of the first member 1202. In other words, when viewed in cross-section, it is a projecting structure, that is supported at one end and carries a load at the other end or along its length. A ramped surface 1214 forms a transition from the groove 1212 to the cup surface 1206. The first flange 1208 includes a protruding first contact rim 1216. "protruding" has the meaning described above, i.e. the contact rim 1216 extends away from the nominal profile of the cup surface 1206 and towards the second member 1204. The first contact rim 1216 may have a straight, curved, or toroidal cross-sectional shape.

The first flange 1208 has an angular offset relative to the balanced centroidal axis N1. In other words, the first flange 1208 is asymmetric to the balanced centroidal axis N1. This is also referred to as a "non-axisymmetric" condition. In the particular example and view shown in FIG. 39, the first flange 1208 is offset to the right side of the figure. The angular offset or asymmetric position allows the functional characteristics of the first flange 1208 to be tailored to specific operating conditions encountered by the prosthetic joint 1200. For example, the angular offset may be selected so that the first flange is aligned with an expected primary load vector.

The interior also includes a cantilevered second flange 1218 which is defined in part by an undercut groove 1222 formed in the first member 1202. The second flange 1218 includes a protruding second contact rim 1224. The second contact rim 1224 may have a straight, curved, or toroidal cross-sectional shape.

The second member 1204 is also made from a rigid material and has a wear-resistant, convex contact surface 1228. The first and second contact rims 1216 and 1224 bear directly against the contact surface 1228 so as to transfer axial and lateral loads from one member to the other while allowing pivoting motion between the two members 1202 and 1204. The annular configuration of contact rims 1216 and 1224 results in a joint configuration which permits only pivoting and rotational motion, and is statically and dynamically determinate for the life of the joint 1200.

Nominally the first and second contact rims 1216 and 1224 define two separate "ring" or "band" contact interfaces with the contact surface 1228 of the second member 1204. The flanges 1208 and 1218 (and thus the contact rims 1216 and 1224) of the first member 1202 are conformable to the contact surface 1228 when the joint 1200 is placed under load. The flanges 1208 and 1218 can conform to the imperfect contact surface 1228 and deflect in an irregular shape, in the manner described above for the joint 1200. Any of the flanges described herein may have free shape defining a first contact area with the contact surface, and a loaded (i.e. deflected) shape defining a second contact area with the contact surface which is substantially larger than the first contact area, substantially reducing the contact stress between the two members. The contact rims 1216 and 1224 and the contact surface 1228 may be configured with curvatures to have an asymmetric wear characteristic as described above in detail.

The facing surfaces of either or both of the first and second members 1202 and 1204 may include a face layer of a known coating such as titanium nitride, chrome plating, carbon thin films, and/or diamond-like carbon coatings, and/or a another substantially thicker wear-resistant material such as ultra-high molecular weight (UHMW) polyethylene. This face layer is used to impart wear resistance, as described above.

Figure 40:
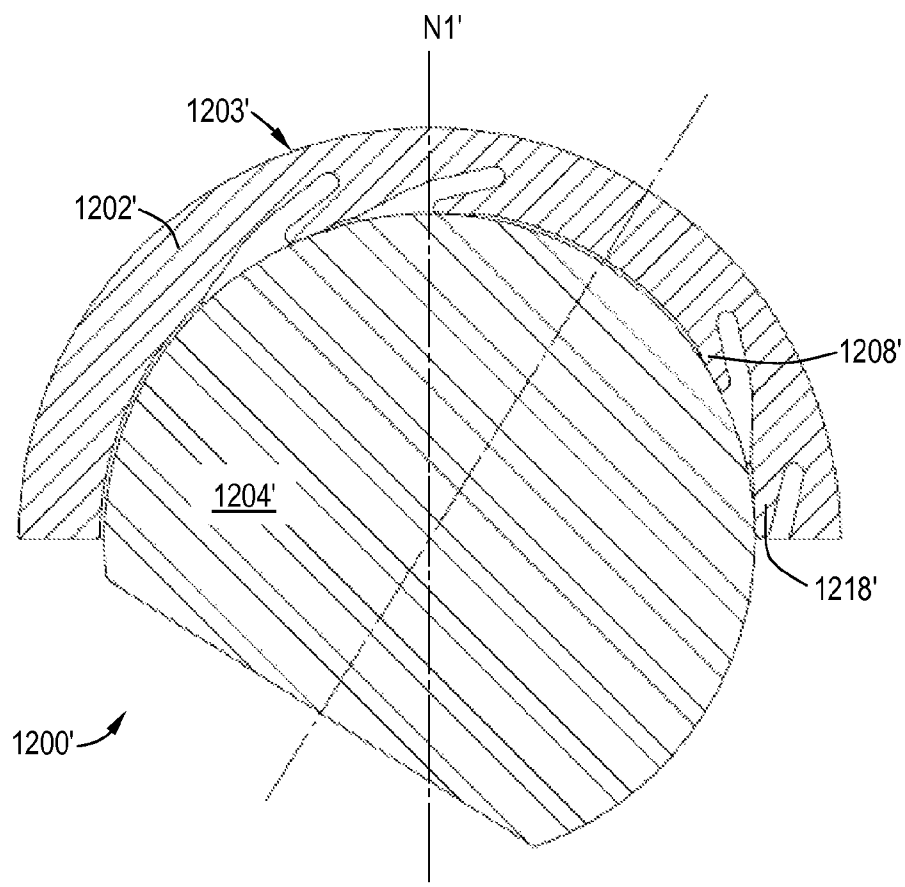
FIG. 40 is a cross-sectional view of a prosthetic joint constructed in accordance with another aspect of the present invention.

Depending on the specific application, the second flange 1218 may have an angular offset like the first flange 1208. For example, FIG. 40 illustrates a prosthetic joint 1200' substantially similar in construction to the prosthetic joint 1200, with first and second members 1202' and 1204'. The first member 1202' has a balanced centroidal axis "N1'", and first and second flanges 1208' and 1218'. The first flange 1208' is angularly offset from the balanced centroidal axis N1' (i.e. it is asymmetric relative to the balanced centroidal axis N1') and the second flange 1218 is also angularly offset from the balanced centroidal N1' (i.e. it is asymmetric relative to the balanced centroidal axis N1').

Figure 41:
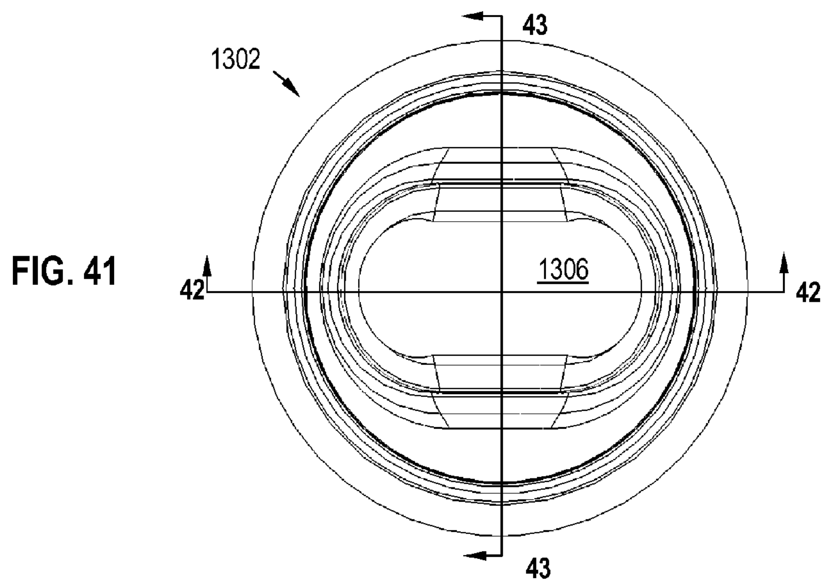
FIG. 41 is a plan view of a portion of a prosthetic joint constructed in accordance with another aspect of the present invention.
Figure 42:
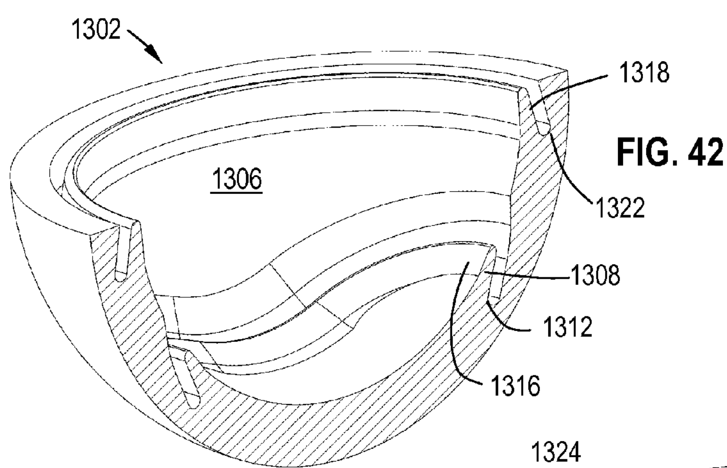
FIG. 42 is a view taken along lines 42-42 of FIG. 41.
Figure 43:
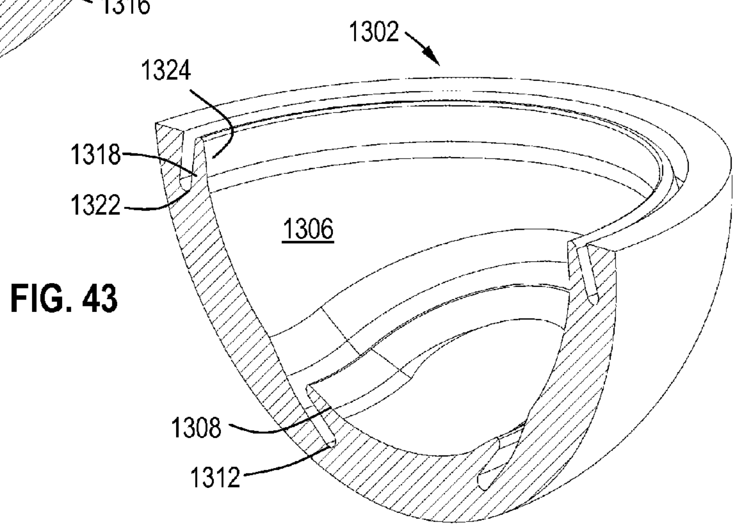
FIG. 43 is a view taken along lines 43-43 of FIG. 41.

The flange of the joint members described above need not be circular, elliptical, or another symmetrical shape in plan view, and need not lie in a single plane. For example, FIGS. 41-43 illustrate a joint member 1302. Its interior defines a cup surface 1306 having a nominal profile. The interior includes a cantilevered first flange 1308, defined in part by an undercut groove 1312 formed in the first member 1302. The first flange 1308 includes a protruding first contact rim 1316. The first contact rim 1316 may have a straight, curved, or toroidal cross-sectional shape. The interior also includes a cantilevered second flange 1318 which is defined in part by an undercut groove 1322 formed in the first member 1302. The second flange 1318 includes a protruding second contact rim

1324. The second contact rim 1324 may have a straight, curved, or toroidal cross-sectional shape.

The first flange 1308 (and therefore the first contact rim 1316) have a "saddle" shape. In this particular example it has a racetrack shape in plan view, and the portions at the ends of the major axis of the racetrack shape are elevated (in the z-direction) relative to the remainder of the shape. The first contact rim 1316 is shaped so as to define a contact band in which some or all points on its surface lie on a sphere (or otherwise match the shape of the mating convex joint member described above). The second flange 1318 could have a similar saddle shape as well.

Figure 44:
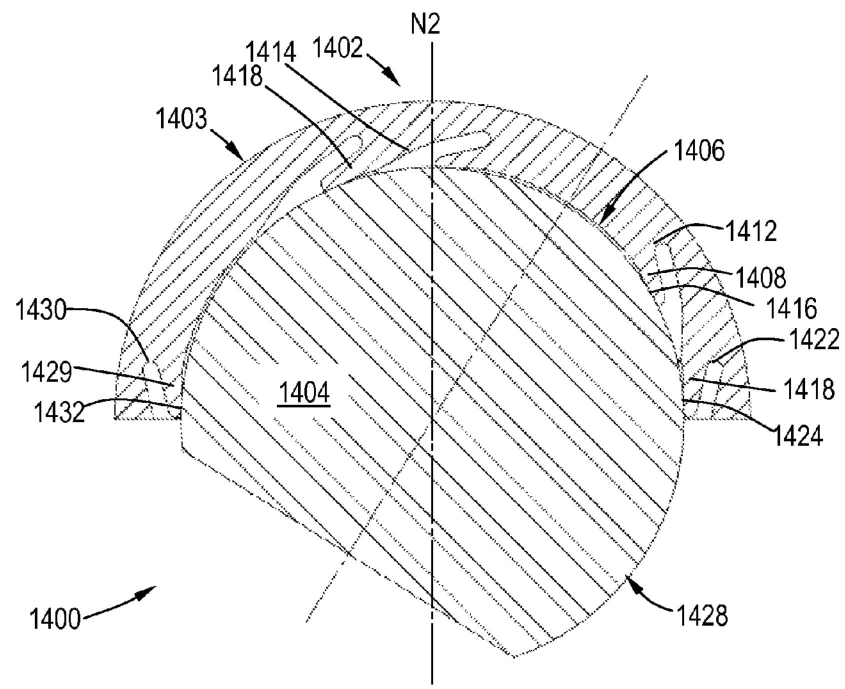
FIG. 44 is a cross-sectional view of a prosthetic joint constructed in accordance with another aspect of the present invention.
Figure 45:
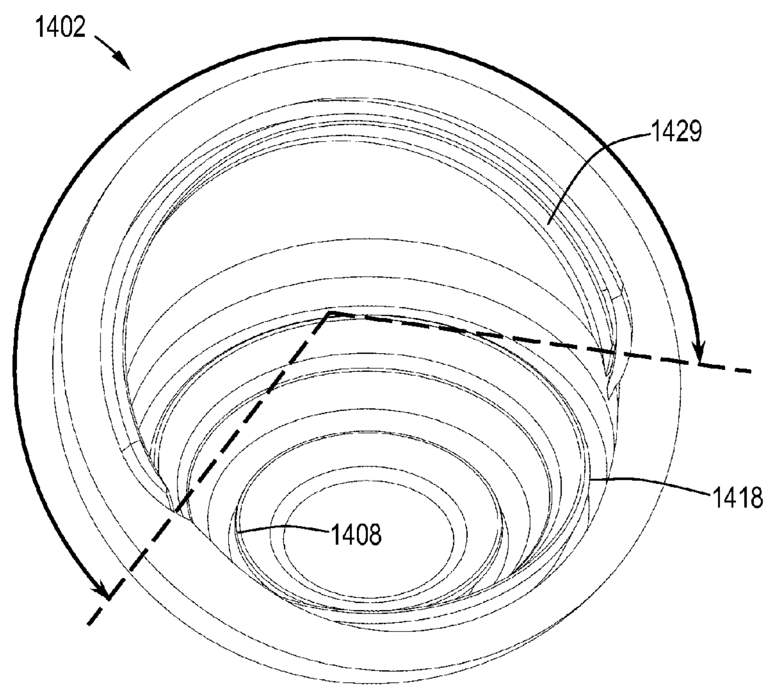
FIG. 45 is a perspective view of the prosthetic joint of FIG. 44.

The prosthetic joints described herein may include one or more flanges with an open perimeter. For example, FIGS. 44 and 45 illustrate another alternative prosthetic joint 1400 comprising first and second members 1402 and 1404. The illustrated prosthetic joint 1400 is generally similar in construction and function to the prosthetic joint 1000 described above, and one or both of the members 1402 and 1404 may bone-implantable as described above.

A balanced centroidal axis "N2", may be considered to pass through the first member 1402. This axis N2 is defined in the same manner as the balanced centroidal axis "N1" described above. The first member 1402 is constructed from a rigid material and may generally be thought of as a "cup", as described above. Its interior defines a cup surface 1406 having a nominal profile. The interior includes a cantilevered first flange 1408, defined in part by an undercut groove 1412 formed in the first member 1402. A ramped surface 1414 forms a transition from the groove 1412 to the nominal cup surface 1406. The first flange 1408 includes a protruding first contact rim 1416. The first contact rim 1416 may have a straight, curved, or toroidal cross-sectional shape.

The first flange 1408 has an angular offset relative to the balanced centroidal axis N2, in other words it is asymmetric relative to the balanced centroidal axis N2. The interior also includes a cantilevered second flange 1418 which is defined in part by an undercut groove 1422 formed in the first member 1402. The second flange 1418 includes a protruding second contact rim 1424. The second contact rim 1424 may have a straight, curved, or toroidal cross-sectional shape.

In the example shown in FIGS. 44 and 45, the second flange 1418 is also angularly offset from the balanced centroidal axis N2, i.e. it is asymmetric relative to the balanced centroidal axis.

The interior also includes a cantilevered third flange 1429 which is defined in part by an undercut groove 1430 formed in the first member 1402. The third flange 1418 includes a protruding third contact rim 1432. The third contact rim 1432 may have a straight, curved, or toroidal cross-sectional shape. As best seen in FIG. 45, the third flange 1429 has an open perimeter, circumscribing less than 360 degrees. The distal ends of the third flange 1429 may be feathered away from the nominal cup surface, for example either by tapering the third flange's thickness or by tilting the distal ends outward relative to the remainder of the flange, so as not to contact the contact surface 1428 of the second member 1404.

The third flange 1429 could be symmetric or asymmetric relative to the balanced centroidal axis N2.

The second member 1402 is also made from a rigid material and has a wear-resistant, convex contact surface 1428. The first, second, and third contact rims 1416, 1424, and 1432, bear directly against the contact surface 1428 so as to transfer axial and lateral loads from one member to the other while allowing pivoting motion between the two members 1402 and 1404.

Nominally the first, second, and third contact rims 1416, 1424, and 1432 define three separate "ring" or "band" contact interfaces with the contact surface 1428 of the second member 1404. The flanges 1408, 1418, and 1429 (and thus the contact rims 1216, 1224, and 1432) of the first member 1402 are conformable to the contact surface 1428 when the joint 1400 is placed under load. The flanges 1408, 1418, and 1429 can conform to the imperfect contact surface 1428 and deflect in an irregular shape, in the manner described above for the joint 1000.

The facing surfaces of either or both of the first and second members 1402 and 1404 may include a face layer of a known coating such as titanium nitride, chrome plating, carbon thin films, and/or diamond-like carbon coatings, and/or a another substantially thicker wear-resistant material such as ultra-high molecular weight (UHMW) polyethylene. This face layer is used to impart wear resistance, as described above.

Figure 46:
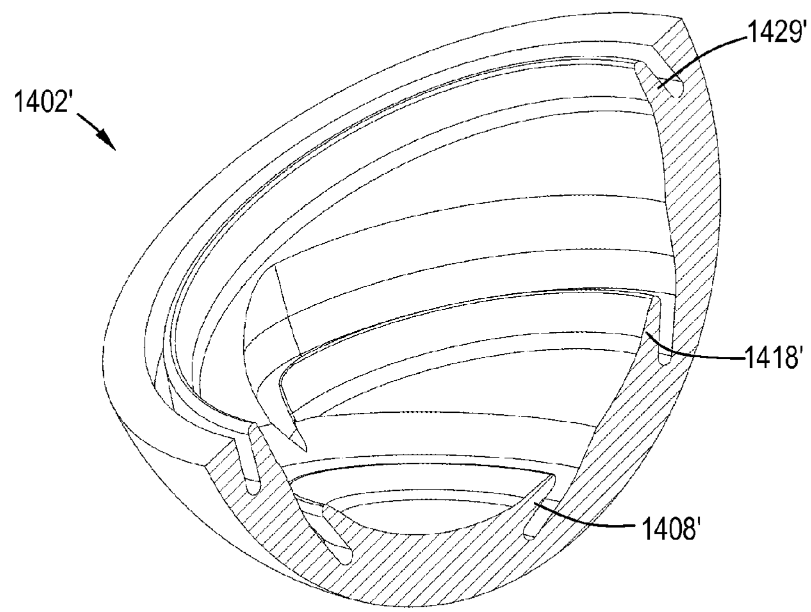
FIG. 46 is a perspective view of a prosthetic joint constructed in accordance with another aspect of the present invention.
Figure 47:
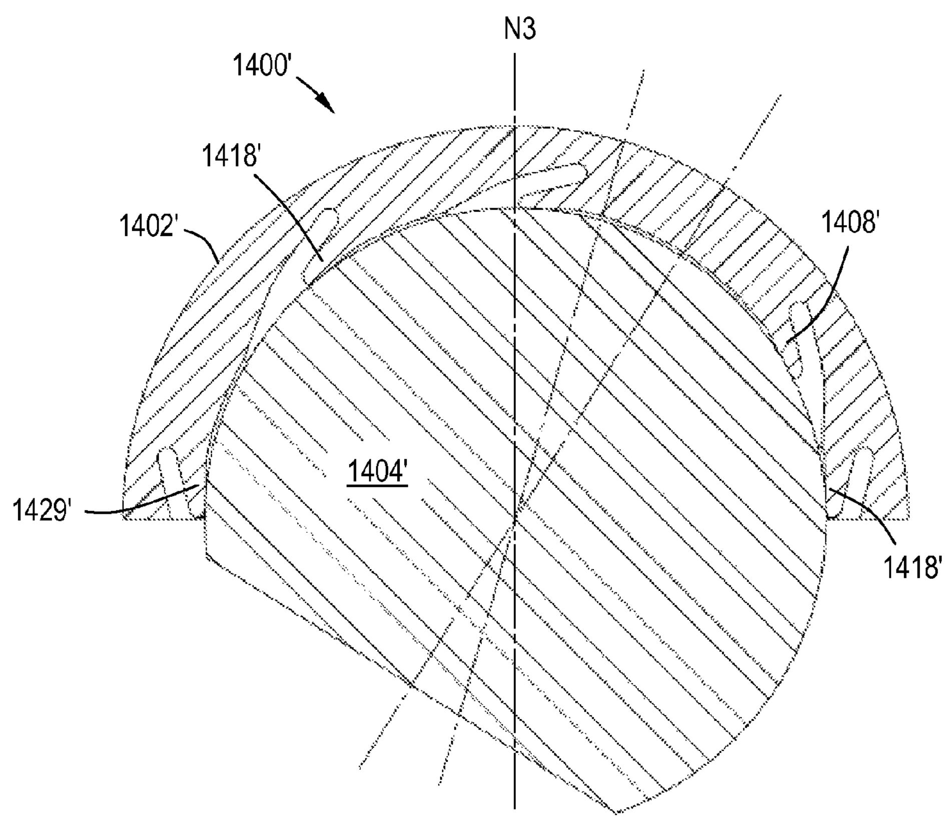
FIG. 47 is a cross-sectional view of the prosthetic joint of FIG. 46.
Figure 48:
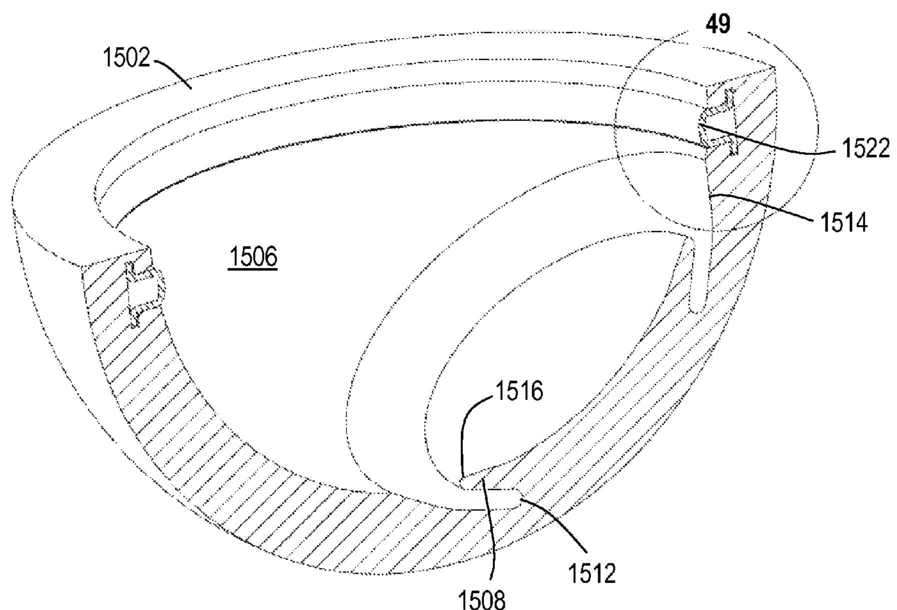
FIG. 48 is a sectional perspective view of a prosthetic joint constructed in accordance with another aspect of the present invention.
Figure 49:
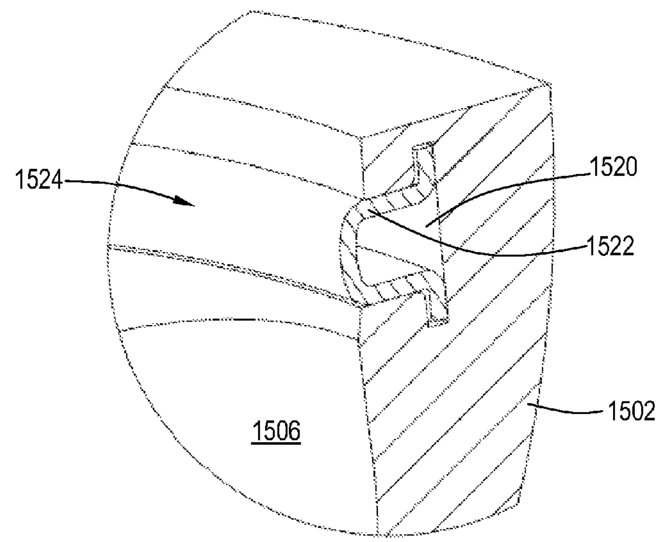
FIG. 49 is an enlarged portion of the joint of FIG. 48, showing a rim configuration thereof.

Any of the flanges may have an open perimeter. For example, FIGS. 46 and 47 illustrate a prosthetic joint 1400' similar in construction to the prosthetic joint 1400, including first and second members 1402' and 1404'. The first member 1402' includes cantilevered first, second, and third flanges 1408', 1418', and 1429'. In this example the first and third flanges 1408' and 1429' have a closed perimeter, and the second flange 1418' has an open perimeter, circumscribing less than 360 degrees. Any or all of the flanges 1408', 1418', and 1429' may be angularly offset from (i.e. asymmetric relative to) a balanced centroidal axis "N3" of the first member 1402', as described above. The construction and function of the joint 1400' is otherwise identical to the joint 1400. As described above for the flange 1429, the distal ends of any flange having an open perimeter may be feathered away from the nominal cup surface, for example either by tapering the flange's thickness or by tilting the distal ends outward relative to the remainder of the flange, so as not to contact the contact surface of opposing member FIGS. 48 and 49 illustrate a prosthetic joint member 1502, which may be used with any of the convex joint members described above.

The member 1502 is constructed from a rigid material and generally has a concave "cup" shape as described above. It may also be bone-implantable as described above. Its interior defines a cup surface 1506 having a nominal profile. The interior includes a cantilevered flange 1508, defined in part by an undercut groove 1512 formed in the first member 1502. A ramped surface 1514 forms a transition from the groove 1512 to the nominal cup surface 1506. The flange 1508 includes a protruding first contact rim 1516. The first contact rim 1516 may have a straight, curved, or toroidal cross-sectional shape. The flange 1508 may include an angular offset relative to a balanced centroidal of the joint member 1502, as described above.

A peripheral groove 1520 is formed in the cup surface 1506. In the example shown in FIGS. 48 and 49, it has a "T"-shaped cross-section. A contact ring 1522 is received in the groove 1520. A part of the contact ring 1522 protrudes from the nominal profile of the cup surface 1506 and defines a second contact rim 1524. In the illustrated example, the contact ring 1522 has "hat section" cross-sectional shape, with distal flanges that are received in the T-shaped groove 1520.

The contact ring 1522 is made of a rigid material and has a wear-resistant surface, as those terms are described above. It is sized and shaped to achieve controlled elastic deflection, and to be conformable in the manner of the flanges described above. Its construction is thin enough to permit bending under working loads, but not so thin as to allow material yield or fatigue cracking. Deflection of the contact ring 1522 is opposed by the elasticity of the contact ring 1522 in bending, as well as the hoop stresses therein. To achieve long life, the contact ring 1522 is sized so that stresses therein will be less than the endurance limit of the material.

Figure 50:
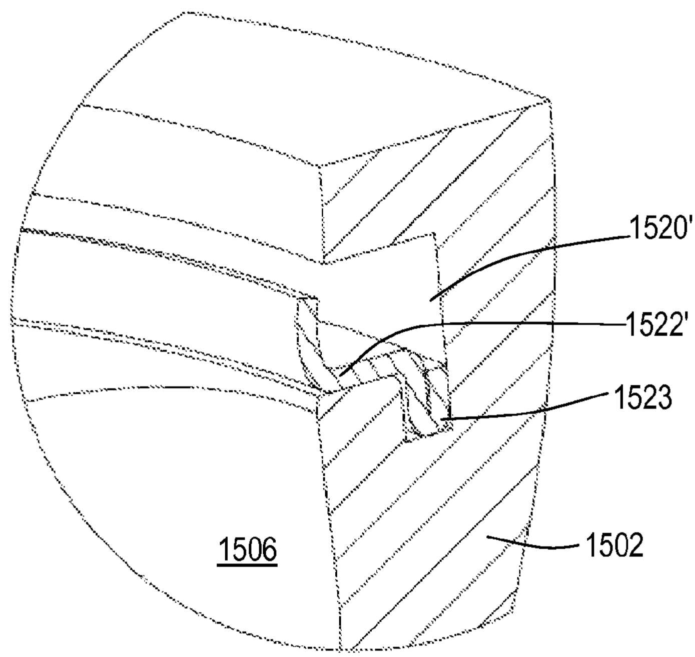
FIG. 50 is a sectional perspective view showing an alternative rim configuration for use with the joint shown in FIG. 49.
Figure 51:
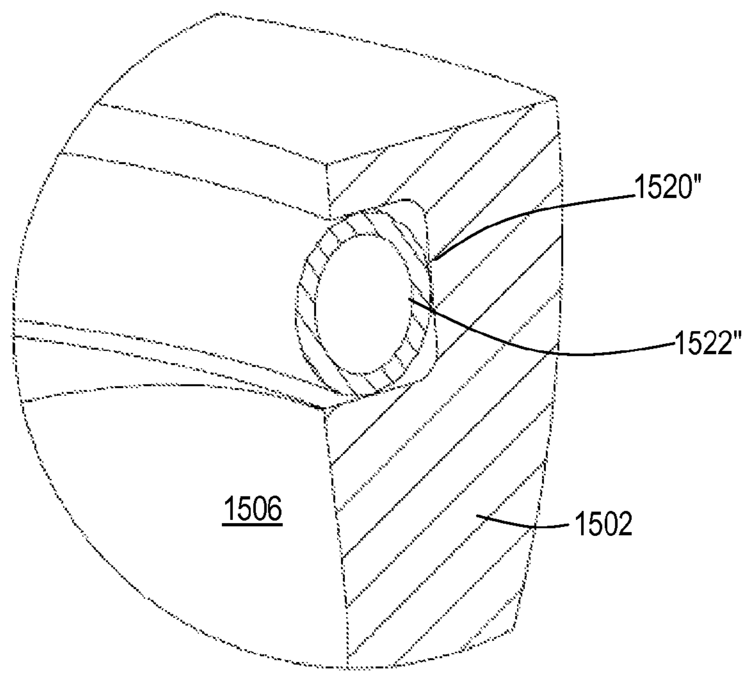
FIG. 51 is a sectional perspective view showing another alternative rim configuration for use with the joint shown in FIG. 49.

Various cross-sectional shapes may be used for the contact ring. For example, FIG. 50 illustrates a contact ring 1522' with a "Z" shape and a doubled-over retention flange 1523. FIG. 51 illustrates a contact ring 1522" with a circular cross-section. The grooves 1520' and 1520" are modified to accommodate their respective contact rings 1522' and 1522".

Nominally the first and second contact rims 1516 and 1524 define two separate "ring" or "band" contact interfaces with the contact surface of the opposed convex member (not shown). The contact rims 1516 and 1524 are conformable to an opposed contact surface when the joint is placed under load.

Figure 52:
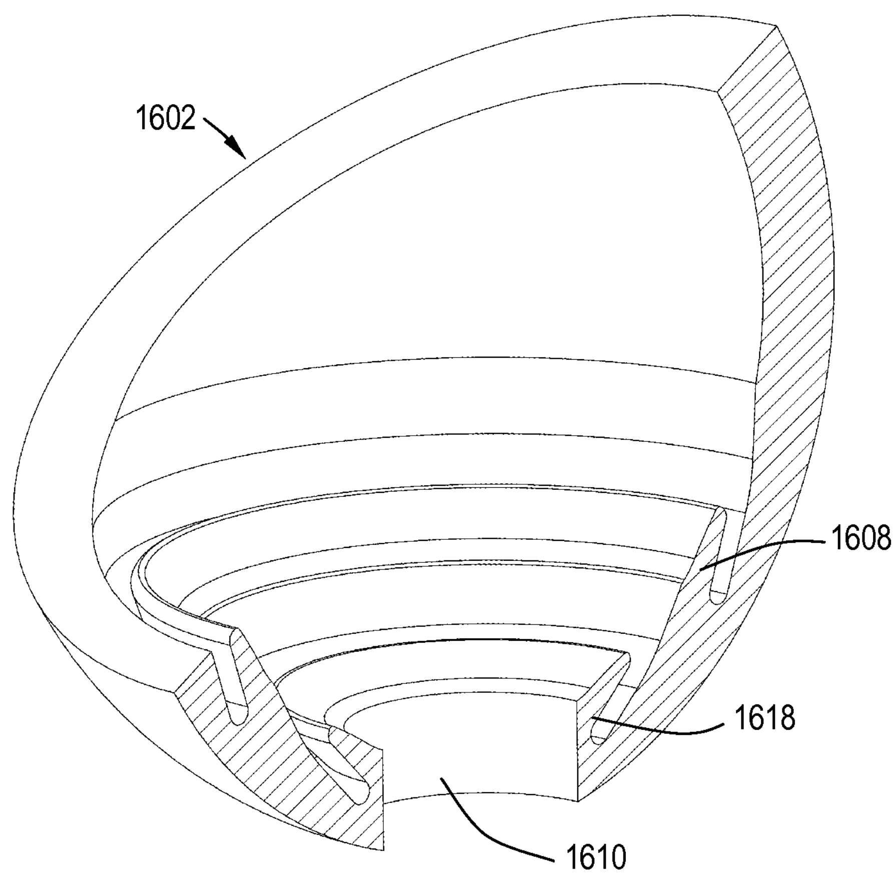
FIG. 52 is a sectional perspective view of a member of a prosthetic joint with an aperture formed therein.

Any of the joint members described above may include holes or apertures formed therein to reduce their weight, or to facilitate manufacture or installation. For example, FIG. 52 illustrates a cup joint member 1602 with first and second flanges 1608 and 1618, and an aperture 1610 formed near the apex of the cup shape.

Figure 53:
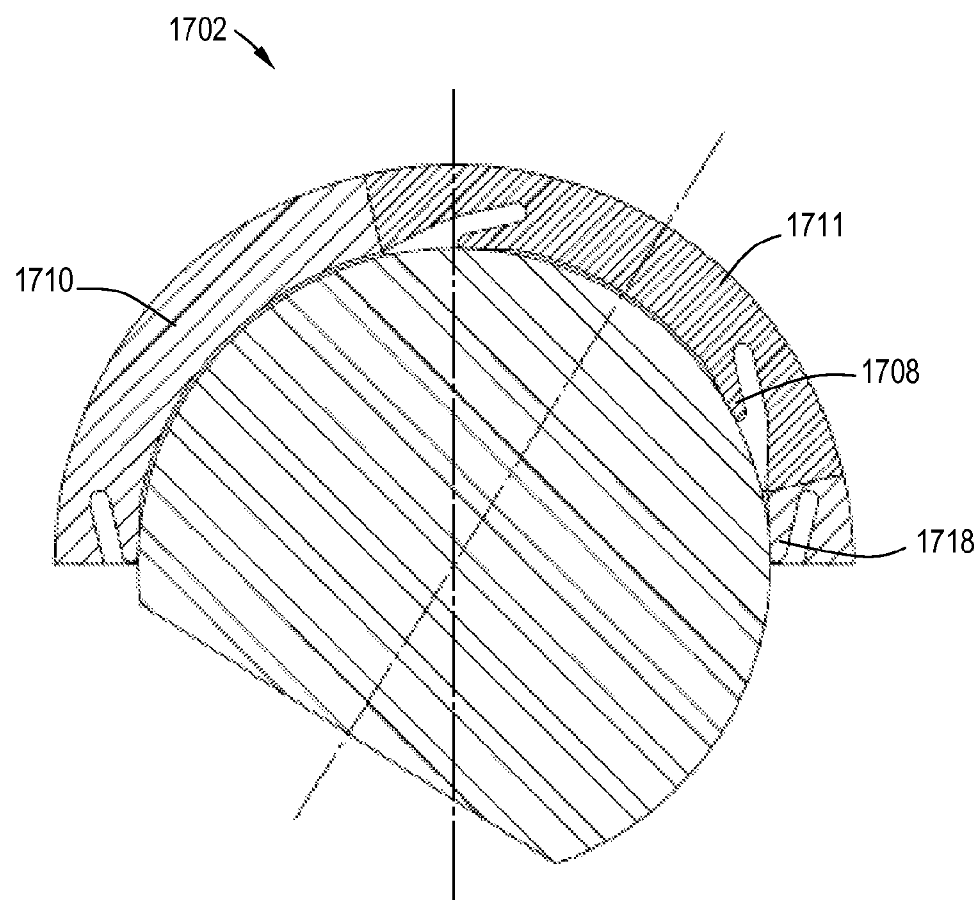
FIG. 53 is a cross-sectional view of a prosthetic joint showing a multi-piece construction.

While the joint members have been illustrated above with monolithic construction, any of the joint members may be made from one or more components built up to form the whole. For example, FIG. 53 illustrates a joint member 1702 which is a cup having a first flange 1708 and a second flange 1718 as described above. The joint member 1702 is made up from an annular first section 1710 and a cap-like second section 1711 which fit together to form the completed cup shape. The two sections 1710 and 1711 are fixed to each other, for example by a mechanical (e.g. interference) fit, an adhesive, welding or other thermal bonding method, or fasteners.

Figure 54:
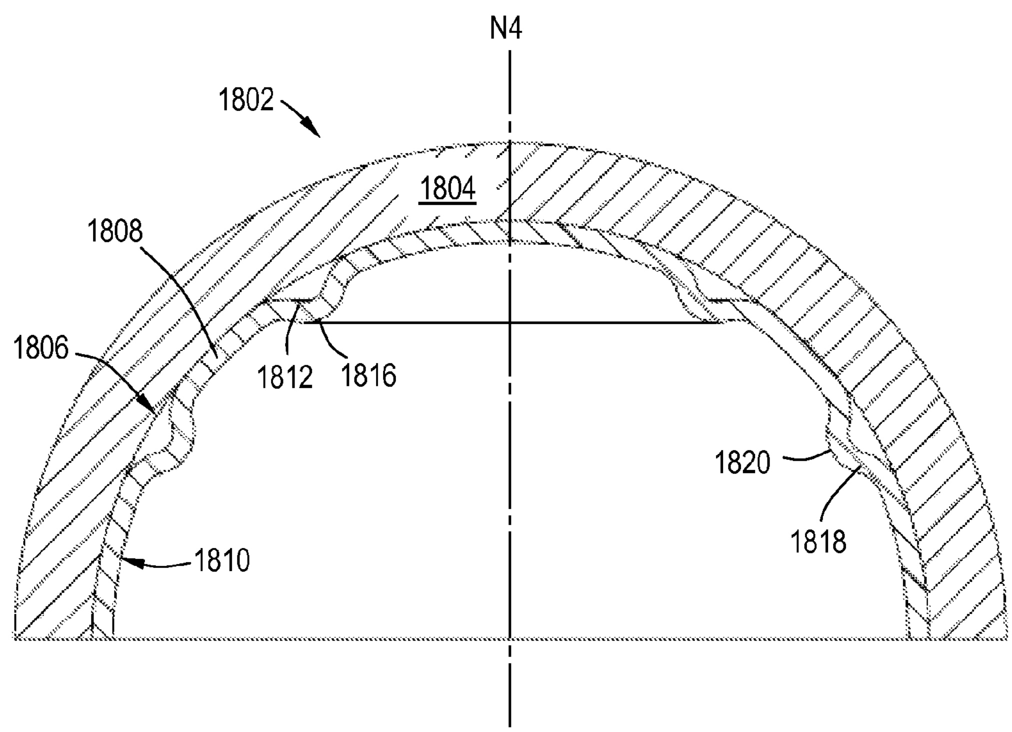
FIG. 54 is a cross-sectional view of a prosthetic joint constructed in accordance with another aspect of the present invention.

FIG. 54 illustrates a prosthetic joint member 1802, which may be used with any of the convex joint members described above.

The member 1802 is constructed from a rigid material and generally has a concave "cup" shape as described above. It may also be bone-implantable as described above. It is made up from a shell 1804 with an interior surface 1806, and a liner 1808 which fits conformally against the interior surface 1806. The liner 1808 may be fixed or moveable relative to the shell 1804. An interior of the liner 1808 defines a nominal cup surface 1810. The liner 1808 includes a first peripheral ring 1812, defined as a generally "U"-shape formed in the liner 1808. The first peripheral ring 1812 includes a protruding first contact rim 1816. The first contact rim 1816 may have a straight, curved, or toroidal cross-sectional shape. The first peripheral ring 1812 may include an angular offset or asymmetric positioning relative to a balanced centroidal axis "N4" of the joint member 1802, as that concept is described above.

The liner 1808 also includes a second peripheral ring 1818, defined as a generally "U"-shape formed in the liner 1808. The second peripheral ring 1818 includes a protruding second contact rim 1820. The second contact rim 1820 may have a straight, curved, or toroidal cross-sectional shape. The second peripheral ring 1818 may include an angular offset relative to a balanced centroidal "N4" of the joint member 1802, as that concept is described above.

The liner 1808 is made of a rigid material and has a wear-resistant surface, as those terms are described above. The first and second peripheral rings 1812 and 1818 are sized and shaped to achieve controlled elastic deflection, and to be conformable in the manner of the flanges described above. Their construction is thin enough to permit bending under working loads, but not so thin as to allow material yield or fatigue cracking Deflection of the contact rings 1812 and 1818 are opposed by the elasticity of the rings in bending, as well as the hoop stresses therein. To achieve long life, the contact rings 1812 and 1818 are sized so that stresses therein will be less than the endurance limit of the material.

Nominally the first and second contact rims 1816 and 1820 define two separate "ring" or "band" contact interfaces with the contact surface of the opposed convex member (not shown). The contact rims 1816 and 1820 are conformable to the opposed contact surface when the joint is placed under load.

As noted above, known coatings such as titanium nitride, chrome plating, carbon thin films, and/or diamond-like carbon coatings may be used to impart wear resistance or augment the wear resistance of any of the contact surfaces and/or contact rims described above. To the same end, it may be desirable to surface treat either or both interfaces of any of the above-described implants or joints with a laser, shot peen, burnishing, or water shock process, to impart residual compressive stresses and reduce wear. The benefit could be as much from surface annealing and microstructure and microfracture elimination as smoothing itself.

The foregoing has described prosthetic joints with wear-resistant properties and conformal geometries. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

What is claimed is:

1. A prosthetic joint, comprising:

(a) first member having a balanced centroidal axis, the first member comprising a rigid material and including a concave interior defining a cup surface, the cup surface including:

(i) a cantilevered flange defined by an undercut in the first member defining a wear-resistant first contact rim which protrudes relative to a nominal profile of the cup surface; and (ii) a contact ring received in a groove formed in the cup surface, the contact ring comprising a rigid material and defining a wear-resistant second contact rim which protrudes relative to the nominal profile of the cup surface;

(b) a second member comprising a rigid material with a wear-resistant, convex contact surface;

(c) where the first and second contact rims bear directly against the contact surface of the second member, so as to transfer axial and lateral loads between the first and second members, while allowing pivoting motion between the first and second members; and (d) wherein the flange and the contact ring are shaped and sized so as to deform elastically and permit the first and second contact rims to conform in an irregular shape to the contact surface, when the joint is placed under a predetermined load.

2. The prosthetic joint of claim 1, wherein at least one of the contact rims has a curved or toroidal cross-sectional shape.

3. The prosthetic joint of claim 1, wherein the surfaces of the first and second members are ceramic, metallic, or a combination thereof.

4. The prosthetic joint of claim 1, where the flange is sized so as to permit elastic deflection of the flange while limiting stresses in the flange to less than the endurance limit of the rigid material of the first member, when a predetermined load is applied to the joint.

5. The prosthetic joint of claim 1, wherein curvatures of the first and second contact rims are different from a curvature of the contact surface.

6. The prosthetic joint of claim 1 wherein curvatures of the first and second contact rims and the contact surface are configured to produce an asymptotic wear characteristic when in use.

7. The prosthetic joint of claim 1 wherein the flange has a plan view shape which is noncircular.

8. The prosthetic joint of claim 1 wherein at least one of the first and second members comprises at least two sections fixed together.

9. The prosthetic joint of claim 1 wherein the flange has an open perimeter.

10. The prosthetic joint of claim 9 wherein distal ends of the flange having the open perimeter are feathered away from the nominal profile of the cup surface, so as not to contact the contact surface of the second member.

11. The prosthetic joint of claim 1 wherein the cup surface includes a second cantilevered flange defining a wear-resistant third contact rim which protrudes relative to the nominal profile of the cup surface.

12. The prosthetic joint of claim 11 wherein the second flange has an open perimeter.

13. The prosthetic joint of claim 1 wherein one or more apertures pass through the first member.

14. The prosthetic joint of claim 11 where the second flange is asymmetric relative to the balanced centroidal axis.

15. The prosthetic joint of claim 1 wherein at least one of the surfaces incorporates a wear-resistant thin film or coating.

16. The prosthetic joint of claim 1 in which at least one of the members is bone-implantable.

17. The prosthetic joint of claim 1 wherein the flange has a free shape defining a first contact area with the contact surface and a loaded shape defining a second contact area with the contact surface which is larger than the first contact area.

18. The prosthetic joint of claim 1 wherein:

the groove has a T-shape cross-sectional shape; and the contact ring has a hat section cross-sectional shape including distal flanges received in the groove.

19. The prosthetic joint of claim 1 wherein the contact ring has a Z-shaped section cross-sectional shape.

20. The prosthetic joint of claim 1 wherein the contact ring has a circular cross-sectional shape.

21. The prosthetic joint of claim 1 wherein the flange is asymmetric relative to the balanced centroidal axis.

* * * * *